US011990772B2

(12) United States Patent
Dearden et al.

(10) Patent No.: US 11,990,772 B2
(45) Date of Patent: May 21, 2024

(54) AUTOMATICALLY-ALIGNING MAGNETIC FIELD SYSTEM

(71) Applicant: The Alfred E. Mann Foundation for Scientific Research, Valencia, CA (US)

(72) Inventors: Brian R. Dearden, Pasadena, CA (US); Justin Cheng-Tsu Loo, San Marino, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 0 days.

(21) Appl. No.: 17/517,518

(22) Filed: Nov. 2, 2021

(65) Prior Publication Data
US 2022/0140664 A1   May 5, 2022

Related U.S. Application Data

(60) Provisional application No. 63/109,476, filed on Nov. 4, 2020.

(51) Int. Cl.
*H02J 50/90* (2016.01)
*A61N 1/378* (2006.01)
(Continued)

(52) U.S. Cl.
CPC ............ *H02J 50/90* (2016.02); *A61N 1/3787* (2013.01); *H01F 38/14* (2013.01); *H02J 50/005* (2020.01);
(Continued)

(58) Field of Classification Search
CPC .......... H02J 50/90; H02J 50/005; H02J 50/10; H02J 50/402; H02J 50/80; H02J 50/70; A61N 1/3787; H01F 38/14
See application file for complete search history.

(56) References Cited

U.S. PATENT DOCUMENTS 6,504,369 B1 * 1/2003 Varjo ............... G01R 33/34053
324/318
7,126,450 B2   10/2006 Baarman et al.
(Continued)

FOREIGN PATENT DOCUMENTS

KR   2014 0129930 A   11/2014
WO   WO 2012/166126 A1   12/2012
WO   WO2021/031444 A1   2/2021

OTHER PUBLICATIONS

Written Opinion issued in related International Application No. PCT/US2021/057772, dated Jun. 30, 2022, 6 pages.
(Continued)

*Primary Examiner* — Daniel Cavallari
*Assistant Examiner* — Brian K Baxter
(74) *Attorney, Agent, or Firm* — Lewis Roca Rothgerber Christie LLP

(57) ABSTRACT

A wireless power transfer system includes a wireless power transfer device. The wireless power transfer device includes a first transmitting coil oriented along a first axis; a second transmitting coil on the first transmitting coil and oriented along a second axis different from the first axis; and a nonmagnetic material magnetically decoupling the first transmitting coil from the second transmitting coil in an area of overlap between the first and second transmitting coils.

24 Claims, 20 Drawing Sheets

(51) Int. Cl.
*H01F 38/14* (2006.01)
*H02J 50/00* (2016.01)
*H02J 50/10* (2016.01)
*H02J 50/40* (2016.01)
*H02J 50/80* (2016.01)

(52) U.S. Cl.
CPC ............ *H02J 50/10* (2016.02); *H02J 50/402* (2020.01); *H02J 50/80* (2016.02)

(56) References Cited

U.S. PATENT DOCUMENTS

| | | |
|---|---|---|
| 7,286,881 B2 | 10/2007 | Schommer et al. |
| 8,138,875 B2 | 3/2012 | Baarman et al. |
| 8,460,816 B2 | 6/2013 | Julstrom et al. |
| 9,855,436 B2 | 1/2018 | Dearden et al. |
| 9,962,085 B2 | 5/2018 | Griffith |
| 10,348,116 B2 | 7/2019 | Arendarik |
| 10,374,460 B2 | 8/2019 | Oshima et al. |
| 10,566,853 B2 * | 2/2020 | Chen .................... H04B 5/0037 |
| 10,650,963 B2 | 5/2020 | Hanabusa et al. |
| 10,811,186 B2 | 10/2020 | Hanabusa et al. |
| 10,960,219 B2 | 3/2021 | Aghassian et al. |
| 11,192,276 B2 | 12/2021 | Lopatin et al. |
| 2003/0090434 A1 | 5/2003 | Masudaya |
| 2012/0235501 A1 | 9/2012 | Kesler et al. |
| 2012/0306282 A1* | 12/2012 | Tan ...................... H04B 5/0037 307/104 |
| 2014/0232330 A1* | 8/2014 | Robertson ............... H02J 50/80 320/108 |
| 2015/0188365 A1* | 7/2015 | Wang .................. H04B 5/0087 307/104 |
| 2016/0365737 A1* | 12/2016 | Vladan .................. H02J 50/10 |
| 2017/0222483 A1* | 8/2017 | Feng ....................... H02J 50/12 |
| 2017/0352475 A1* | 12/2017 | Ishida .................. H01F 27/292 |
| 2017/0354344 A1* | 12/2017 | Schmale ............. A61B 5/0515 |
| 2018/0019624 A1* | 1/2018 | Chen ....................... H02J 50/12 |
| 2018/0048177 A1* | 2/2018 | Huang .................. H01F 41/041 |
| 2018/0254671 A1* | 9/2018 | Murata ................. H04W 52/42 |
| 2018/0286578 A1* | 10/2018 | Hanabusa ............... H02J 50/70 |
| 2018/0358815 A1* | 12/2018 | Li ....................... H01M 50/213 |
| 2019/0263057 A1 | 8/2019 | Beetz |
| 2019/0331937 A1 | 10/2019 | Owens et al. |
| 2019/0331938 A1* | 10/2019 | Owens .................... H02J 50/10 |
| 2019/0393710 A1* | 12/2019 | Kim ........................ H02J 50/90 |
| 2020/0027653 A1* | 1/2020 | Terauchi ............... H01F 41/046 |
| 2020/0076241 A1* | 3/2020 | Tandai ................... H02J 50/80 |
| 2020/0136435 A1* | 4/2020 | Mitomo ................. H02J 50/402 |
| 2020/0204013 A1* | 6/2020 | Chen ....................... H02J 50/10 |
| 2021/0027928 A1* | 1/2021 | Patel ..................... H01F 27/255 |
| 2021/0152027 A1* | 5/2021 | Kanakasabai ........... H02J 50/40 |
| 2022/0060057 A1* | 2/2022 | Hao ........................ H02J 50/70 |
| 2023/0077596 A1* | 3/2023 | Hurwitz ................. H02J 50/80 320/108 |

OTHER PUBLICATIONS

International Search Report and Written Opinion issued in related International Application No. PCT/US2021/057772, dated Feb. 8, 2022, 12 pages.

Finkenzeller, "Battery powered tags for ISO/IEC 14443, actively emulating load Modulation", *RFID SysTech 2011 7th European Workshop on Smart Objects: Systems, Technologies and Applications* (2011), retrieved from http://www.rfid-handbook.de/downloads/Active-load-modulation_Finkenzeller_20110413_final.pdf (retrieved on Mar. 7, 2022), 8 pages.

Zhangwei Chen et al., 3D printing of ceramics: A review, Journal of the European Ceramic Society, Nov. 6, 2018, 27 pages.

Thomas Hanemann et al., 3D Printing of ABS Barium Ferrite Composites, Materials, Mar. 24, 2020, 13 pages.

Lanbing Liu et al., UV-curable Ferrite Paste for Additive Manufacturing of Power Magnetics, IEEE Magnetics Letters, 2018, 5 pages.

Maria Väätäjä et al., 3D printed dielectric ceramic without a sintering stage, Scientific Reports, Oct. 29, 2018, 8 pages.

Yunqi Wang et al., 3D Printing of NiZn ferrite/ABS Magnetic Composites for Electromagnetic Devices, Cambridge University Press, Jul. 1, 2015, 5 pages.

International Preliminary Report on Patentability issued in related International Application No. PCT/US2021/057772, dated Mar. 6, 2023, 6 pages.

* cited by examiner

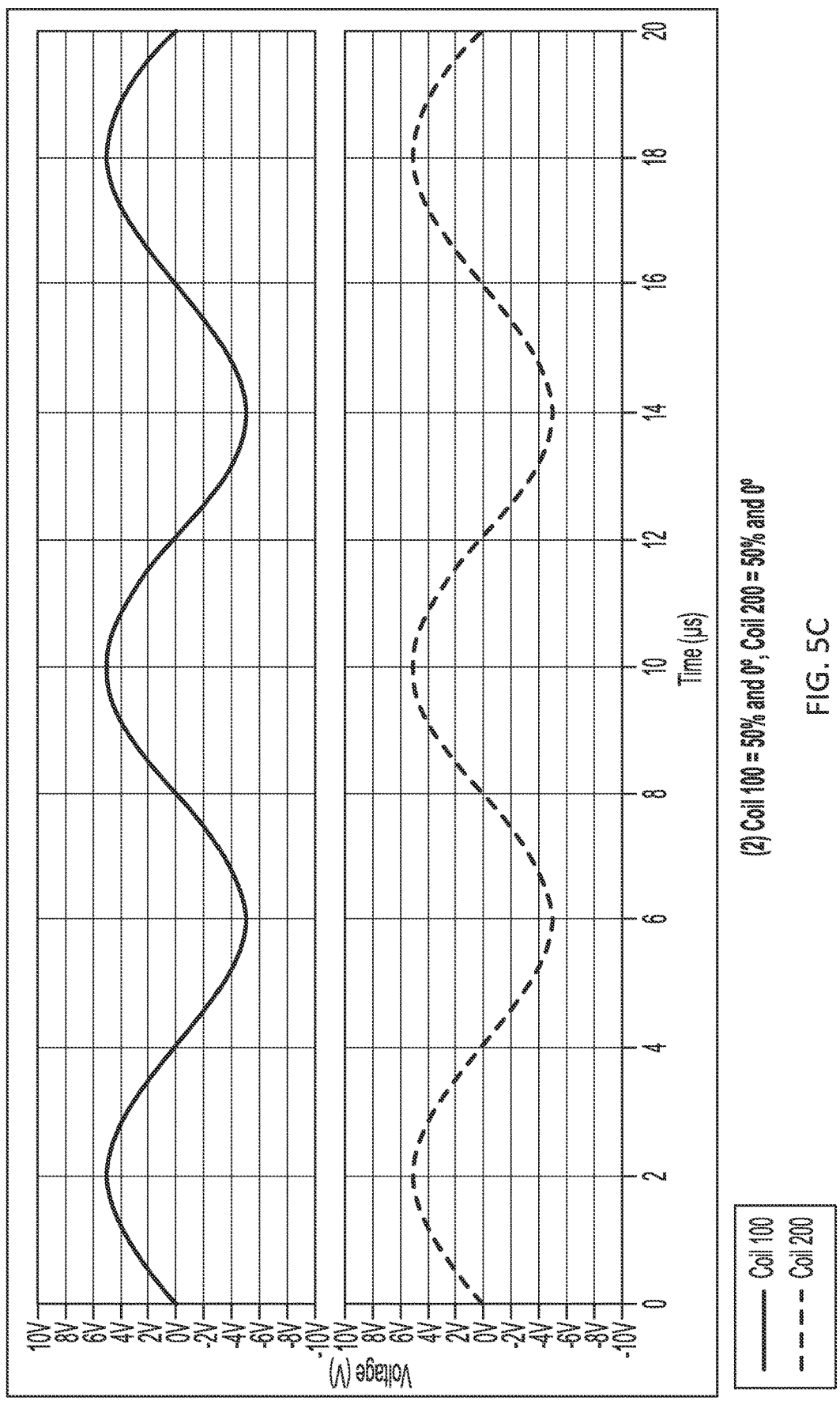

AUTOMATICALLY-ALIGNING MAGNETIC FIELD SYSTEM

CROSS-REFERENCE TO RELATED APPLICATION

This application claims priority to and the benefit of U.S. Provisional Application No. 63/109,476, filed on Nov. 4, 2020, the entire content of which is hereby incorporated by reference.

BACKGROUND

1. Field

The present disclosure relates to a wireless power transfer device configured to generate a magnetic field and control a direction of the magnetic field.

2. Description of the Related Art

A primary coil may be driven with AC current to generate an oscillating magnetic field, and the magnetic field can generate a current in a secondary coil in proximity to the primary coil via electromagnetic induction. Electromagnetic induction can be used to wirelessly transfer energy and is utilized in various industries and devices such as electric vehicles, medical devices, and electronic devices. The magnitude of the current generated in the secondary coil, and thus the effectiveness of the primary coil in transferring energy to the secondary coil, depends on how aligned the magnetic field is with the secondary coil. However, in conventional devices, the primary coil cannot control the direction of the magnetic field, and improving alignment between the magnetic field with the secondary coil requires physically moving and/or orientating the primary coil or the secondary coil, which may be inconvenient and cumbersome.

SUMMARY

The present disclosure relates to various embodiments of a wireless power transfer system including a wireless power transfer device. In one embodiment, the wireless power transfer device includes a first transmitting coil oriented along a first axis; a second transmitting coil on the first transmitting coil and oriented along a second axis different from the first axis; and a nonmagnetic material magnetically decoupling the first transmitting coil from the second transmitting coil in an area of overlap between the first and second transmitting coils.

The present disclosure relates to various embodiments of a method of transmitting power to an electronic device. In one embodiment, the method includes generating a magnetic field by driving, with AC current, at least one selected from a first transmitting coil of a wireless power transfer device oriented along a first axis, and a second transmitting coil of the wireless power transfer device on the first transmitting coil and oriented along a second axis different from the first axis, a nonmagnetic material magnetically decoupling the first transmitting coil from the second transmitting coil being in an area of overlap between the first and second transmitting coils.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter.

BRIEF DESCRIPTION OF THE DRAWINGS

The accompanying drawings, together with the specification, illustrate example embodiments of the present invention. These drawings, together with the description, serve to better explain aspects and principles of the present invention.

FIGS. 5B-5F show graphs of the voltages applied to the first and second transmitting coils as a function of time for the five states of FIG. 5A.

DETAILED DESCRIPTION

Figure 1:
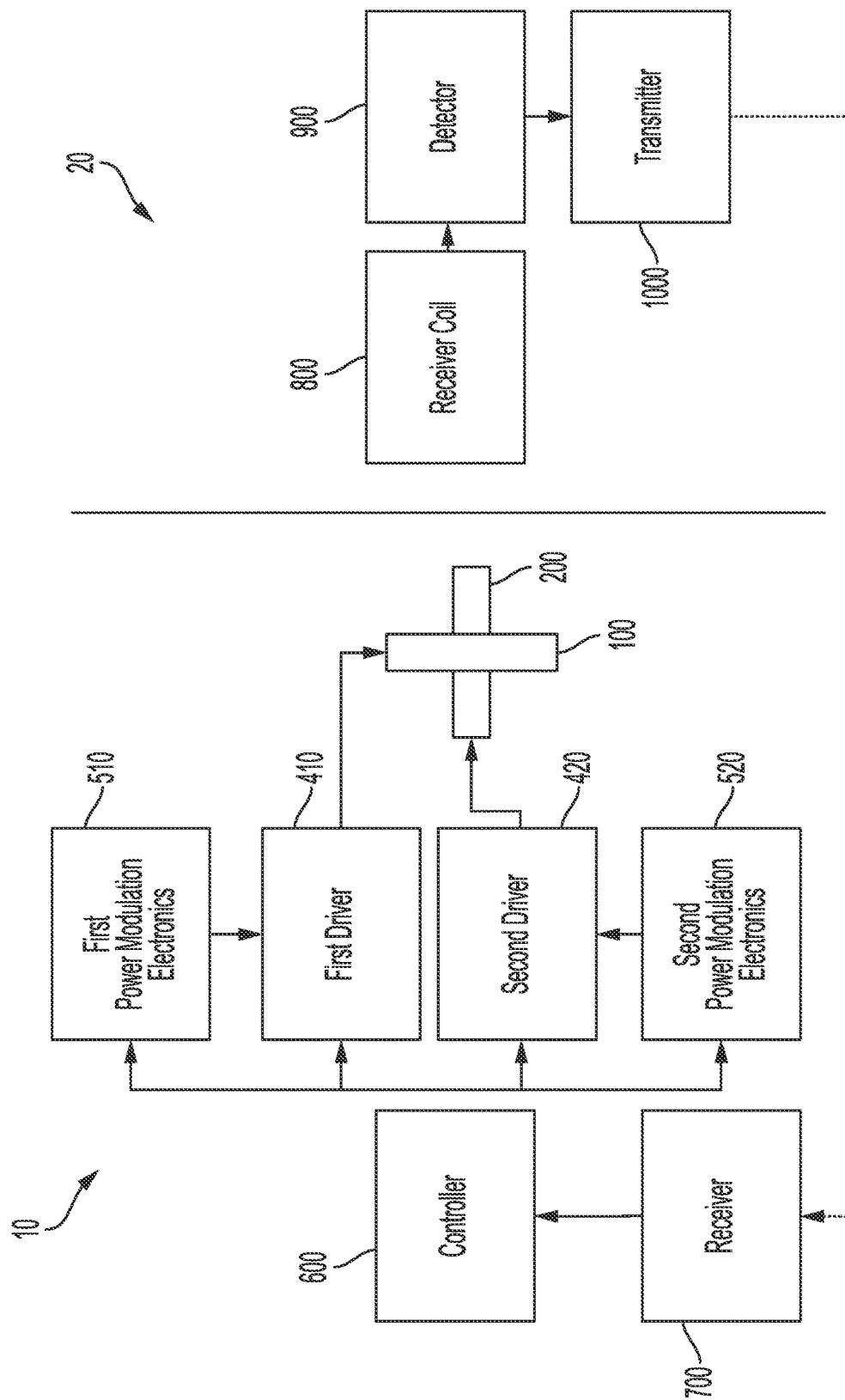
FIG. 1 shows a schematic view of a wireless power transfer system according to some embodiments.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. As used herein, the term "and/or" includes any and all combinations of one or more of the associated listed items.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section, without departing from the spirit and scope of the present disclosure.

It will be understood that when an element or layer is referred to as being "on", "connected to", "coupled to", or "adjacent to" another element or layer, it can be directly on, connected to, coupled to, or adjacent to the other element or layer, or one or more intervening element(s) or layer(s) may be present. In contrast, when an element or layer is referred to as being "directly on," "directly connected to", "directly coupled to", or "immediately adjacent to" another element or layer, there are no intervening elements or layers present.

As used herein, the term "substantially" and similar terms are used as terms of approximation and not as terms of degree, and are intended to account for the inherent deviations in measured or calculated values that would be recognized by those of ordinary skill in the art. Also, the terms "about," "approximately," and similar terms, when used herein in connection with a numerical value or a numerical range, are inclusive of the stated value and mean within an acceptable range of deviation for the particular value as determined by one of ordinary skill in the art, considering the measurement in question and the error associated with measurement of the particular quantity (e.g., the limitations of the measurement system). For example, "about" may mean within one or more standard deviations, or within ±30%, 20%, 10%, 5% of the stated value.

Example embodiments of the present disclosure will now be described with reference to the accompanying drawings. In the drawings, the same or similar reference numerals refer to the same or similar elements throughout. As used herein, the use of the term "may," when describing embodiments of the present disclosure, refers to "one or more embodiments of the present disclosure."

FIG. 1 schematically illustrates a wireless power transfer system according to some embodiments. The wireless power transfer system may include a wireless power transfer device 10 and an electronic device 20.

The wireless power transfer device 10 may include a first transmitting coil 100, a second transmitting coil 200 on (e.g., positioned on) the first transmitting coil 100, a driver 400 configured to drive the first transmitting coil 100 with a first AC current and the second transmitting coil 200 with a second AC current, power modulation electronics 500 configured to modulate the first and second AC currents provided by the driver 400, a controller 600 (e.g., a microcontroller) configured to control the operations of the driver 400 and the power modulation electronics 500, and a receiver 700 for receiving information (e.g., information transmitted by the electronic device 20).

The electronic device 20 may include a receiver coil 800, a detector 900 configured to detect information about power received in the receiver coil 800, and a transmitter 1000 configured to transmit information (e.g., transmit information to the wireless power transfer device 10). In some embodiments, the transmitter 1000 may be a radio or an RF transmitter.

The wireless power transfer device 10 may be configured to generate an oscillating magnetic field by driving the first and second transmitting coils 100 and 200 with the first and second AC currents, respectively, and to rotate the direction of the magnetic field by controlling (e.g., setting or adjusting) a first magnitude of the first AC current, a second magnitude of the second AC current, and a phase difference between the first and second AC currents (e.g., the wireless power transfer device 10 is configured to rotate the direction of the magnetic field by differentially driving the first and second transmitting coils 100 and 200). When the wireless power transfer device 10 generates the magnetic field and the electronic device 20 is in the proximity to the wireless power transfer device 10, a current may be generated in the receiver coil 800 by electromagnetic induction (e.g., wireless resonant induction). The detector 900 may be configured to detect information (e.g., power, amplitude, etc.) about the current generated in the receiver coil 800, and the transmitter 1000 may transmit (e.g., wirelessly transmit) the detected information to outside of the electronic device 20, for example, to the receiver 700 of the wireless power transfer device 10. The controller 600 may control the driver 400 and the power modulation electronics 500 based on the information received by the receiver 700 to control the direction of the magnetic field at the receiver coil 800.

Figure 2:
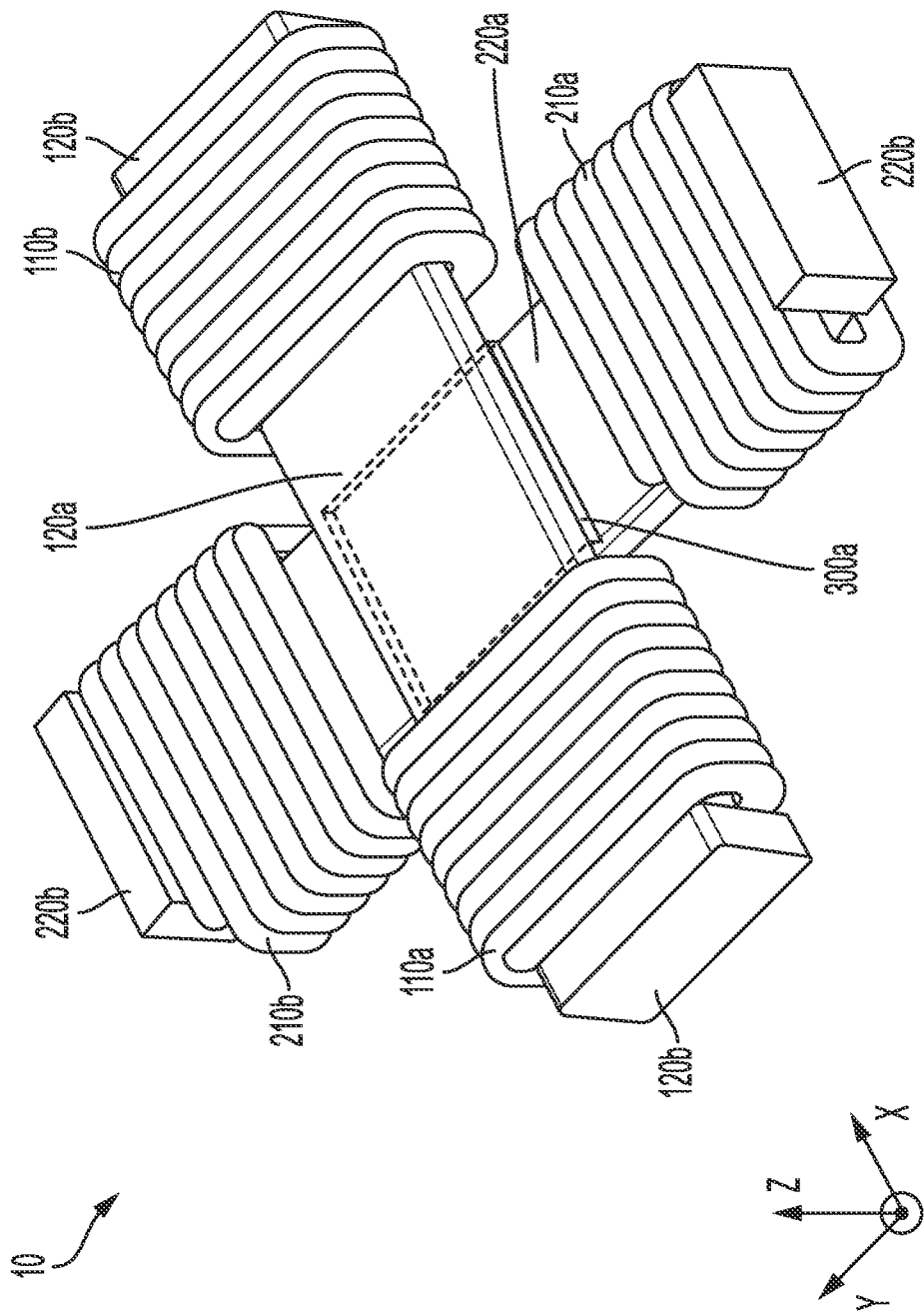
FIG. 2 shows a perspective view of first and second transmitting coils of a wireless power transfer device according to some embodiments.
Figure 3:
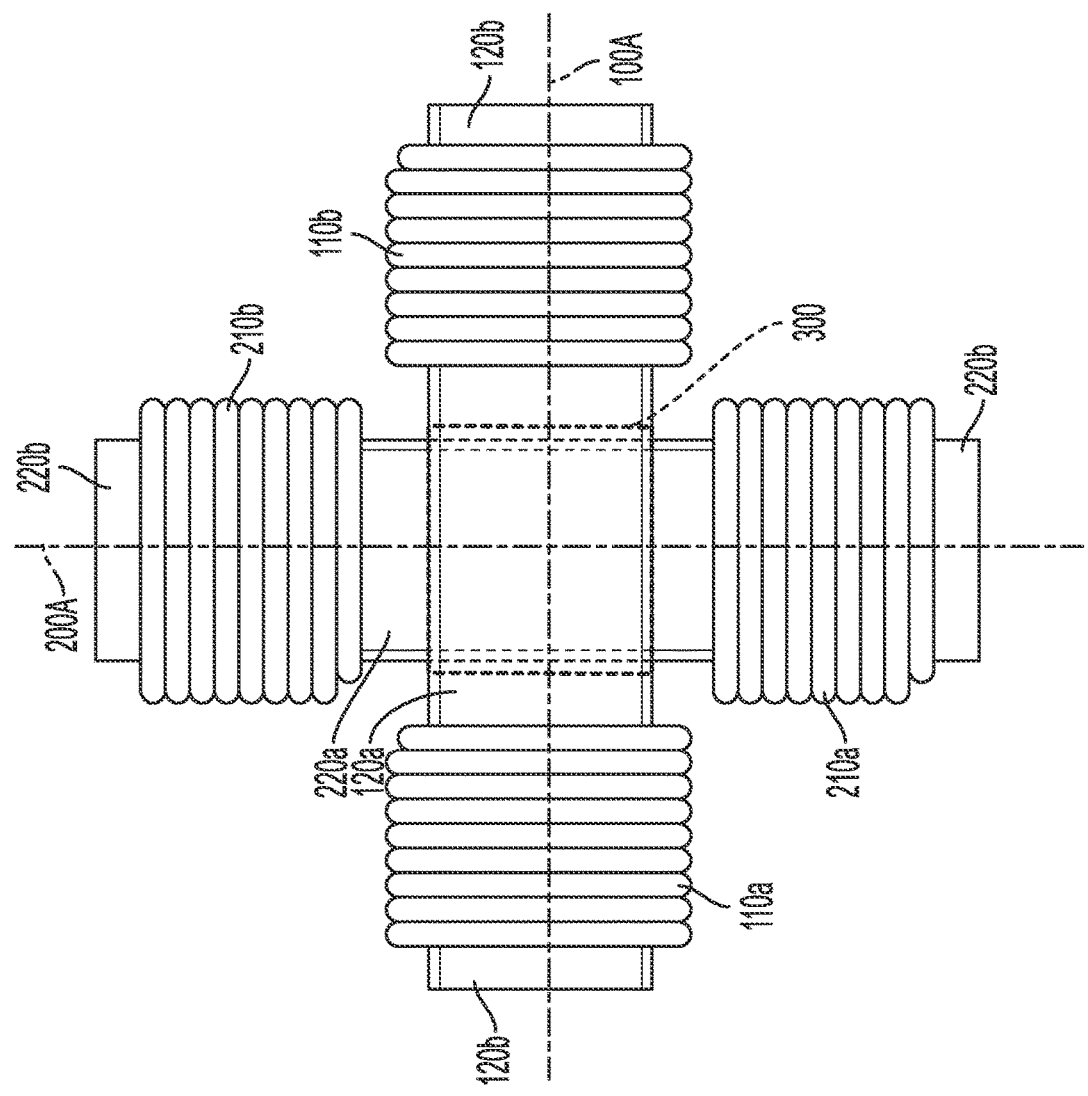
FIG. 3 shows a plan view of the first and second transmitting coils of FIG. 2.
Figure 4:
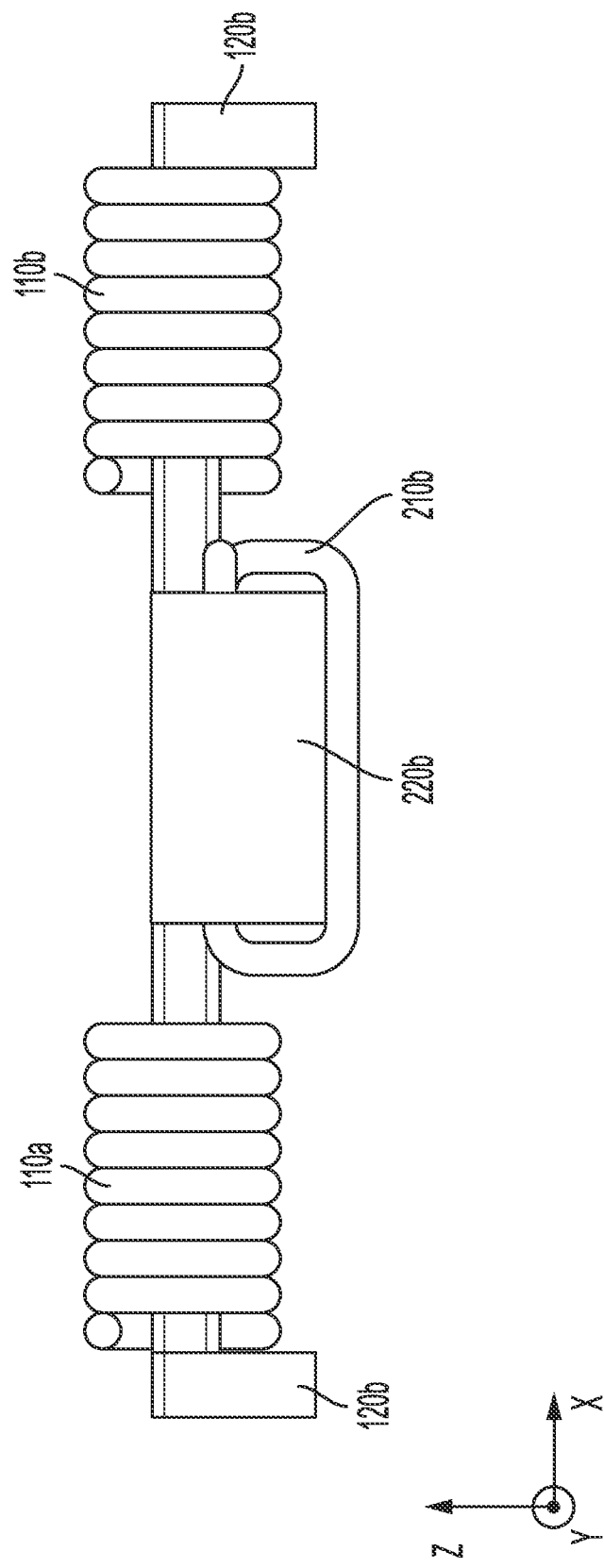
FIG. 4 shows a side view of the first and second transmitting coils of FIG. 2.

The first and second transmitting coils 100 and 200 will now be described in more detail with reference to FIGS. 2-4. FIG. 2 shows a perspective view of the first and second transmitting coils 100 and 200 according to some embodiments, FIG. 3 shows a plan view of the first and second transmitting coils 100 and 200 of FIG. 2, and FIG. 4 shows a side view of the first and second transmitting coils 100 and 200 of FIG. 2.

The first transmitting coil 100 may include a first rod 120 and a first wire 110 wound around the first rod 120, and the second transmitting coil 200 may include a second rod 220 and a second wire 210 wound around the second rod 220.

The first transmitting coil 100 may be aligned along a first axis 100A, and the second transmitting coil 200 may be aligned along a second axis 200A different from the first axis 100A. In some embodiments, the second axis 200A is perpendicular (or substantially perpendicular) to the first axis 100A. That is, an angle between the second axis 200A and the first axis 100A may be approximately (about) 90°. When the first and second axes 100A and 200A are perpendicular, coupling between the first and second transmitting coils 100 and 200 may be reduced or substantially prevented. Coupling between the first and second transmitting coils 100 and 200 may be at a maximum when the first and second axes 100A and 200A are parallel, and coupling between the first and second transmitting coils 100 and 200 may decrease as an angle between the first and second axes 100A and 200A increases towards 90°, at which point coupling is at a minimum. However, the angle between the first axis 100A and the second axis 200A may be any suitable angle, for example, within the range of about 45° to about 90°. In FIGS. 2-4, the first axis 100A is shown as being aligned along an X-axis, and the second axis 200A is shown as being aligned along a Y-axis.

The second transmitting coil 200 may be on (e.g., above) the first transmitting coil 100 and may overlap the first transmitting coil 100 in a plan view (shown in FIG. 3) at an area of overlap 300. In some embodiments, the area of overlap 300 corresponds to a center region of the first transmitting coil 100 and a center region of the second transmitting coil 200. The second transmitting coil 200 may be spaced apart (e.g., separated) from the first transmitting coil 100 in a thickness direction (e.g., a Z-axis direction) at the area of overlap 300.

An intermediate space 300a between the first and second transmitting coils 100 and 200 in the area of overlap 300 may include (e.g., be filled or at least partially filled with) a nonmagnetic material having a low permeability, for example, air, plastic, foam, one or more non-ferrimagnetic materials, one or more low permeability metals (e.g., aluminum and/or copper), etc. In some embodiments, when the intermediate space 300a is filled with air, a frame or housing may be utilized to hold the first and second transmitting coils 100 and 200 and/or to maintain the relative positions of the first and second transmitting coils 100 and 200 with respect to each other. In some embodiments, the material in the intermediate space 300a has a relative permeability of equal to or less than about 5, for example, in the range of about 1 to about 1.5. In some embodiments, the material in the intermediate space 300a may be diamagnetic (e.g., a material having a relative permeability in the range of about 0 to about 1). Therefore, in some embodiments, the second transmitting coil 200 does not contact the first transmitting coil 100, and the first and second transmitting coils 100 and 200 are magnetically independent (e.g., magnetically decoupled and/or magnetically isolated from each other) and/or electrically independent (e.g., electrically decoupled and/or electrically isolated) from each other. Because the first and second transmitting coils 100 and 200 are not in contact, coupling between the first and second transmitting coils 100 and 200 may be reduced or substantially prevented. That is, the first transmitting coil 100 may generate a first magnetic field without being significantly influenced by the presence of the second transmitting coil 200, and the second transmitting coil 200 may generate a second magnetic field without being significantly influenced by the presence of the first transmitting coil 100. A magnetic field generated by the wireless power transfer device 10 may be a superposition of the first and second magnetic fields generated by the first and second transmitting coils 100 and 200, respectively.

The first rod 120 may include a magnetic material having a high permeability, such as a ferrimagnetic material (e.g., soft ferrite material), such as nickel- or manganese-based ferrites (e.g., MnZn, NiZn, and/or the like). The magnetic material may increase the intensity of a magnetic field generated by the first transmitting coil 100 compared to an otherwise comparable coil without the magnetic rod. In some embodiments, the material of the first rod 120 may have a relative permeability equal to or greater than about 5, for example, in the range of about 10 to about 10,000. The second rod 220 may include any material that the first rod 120 may include, and the second rod 220 may include a material that is the same as, or different from, a material included in the first rod 120. In some embodiments, a ratio of the permeability of a material in the first rod 120 to the permeability of the material in the intermediate space 300a may be equal to or greater than approximately (about) 5. When the permeability of the materials of the first and second rods 120 and 220 are significantly larger than the permeability of the material in the intermediate space 300a, coupling between the first and second transmitting coils 100 and 200 may be reduced or substantially prevented. For example, a magnetic field flowing through the first rod 120 may be blocked (by the material in the intermediate space 300a) from permeating through the intermediate space 300a and into the magnetic material of the second rod 220. Thus, the presence of the second transmitting coil 200 may not substantially affect the first magnetic field generated by the first transmitting coil 100, and vice versa.

The first rod 120 may include a first main rod 120a and first thick portion (e.g., a tab or a flange) 120b at an end (e.g., both ends) of the first main rod 120a, and the second rod 220 may include a second main rod 220a and a second thick portion (e.g., a tab or a flange) 220b at an end (e.g., both ends) of the second main rod 220a. The first main rod 120a may have any suitable shape. The second main rod 220a may have any shape that the first main rod 120a may have, and the shape of the second main rod 220a may be the same as, or different from, the shape of the first main rod 120a. In some embodiments, the first main rod 120a has a cylindrical shape. In other embodiments, the first main rod 120a has a rectangular shape having a length along the X-axis, a width along the Y-axis, and a thickness along the Z-axis. The width of the first main rod 120a may be less than the length of the first main rod 120a, and the thickness of the first main rod 120a may be less than the width of the first main rod 120a, but the present disclosure is not limited thereto.

A thickness of the intermediate space 300a may be relatively small compared to the dimensions of the first and second transmitting coils 100 and 200. For example, the thickness of the intermediate space 300a may be less than the length, the width, and/or the thickness of the first main rod 120a. Because the first and second magnetic fields generated by the first and second transmitting coils 100 and 200 will each generally decrease in magnitude as respective distances from the first and second transmitting coils 100 and 200 increase, it is advantageous for the thickness of the intermediate space 300a to be small in order to minimize or at least reduce a disparity between a distance between the electronic device 20 and the first transmitting coil 100 and a distance between the electronic device 20 and the second transmitting coil 200. When the disparity is large, one of the first and second transmitting coils 100 and 200 may have an unintended disproportionate effect on the electronic device 20 compared to the other one of the first and second transmitting coils 100 and 200. Accordingly, in one or more embodiments, the thickness of the intermediate space 300a may be sufficiently small such that the first and second transmitting coils 100 and 200 are substantially coplanar to advantageously minimize or at least reduce the disproportionate effect of one of the first and second transmitting coils 100 and 200 on the electronic device 20.

In some embodiments, a thickness of the first main rod 120a at the area of overlap 300 is less than a thickness of the first main rod 120a at an area outside of the area of overlap 300. For example, the first main rod 120a may have an indent or recess (e.g., a step) at the area of overlap 300 that faces the second main rod 220a. When one or both of the first and second main rods 120a and 220a have such an indent or recess, the distance between the first and second transmitting coils 100 and 200 may be reduced. In some embodiments, the indent or recess in one or both of the first and second main rods 120a and 220a may allow the first and second wires 110 and 210 to be coplanar (or substantially coplanar).

The first thick portion 120b may be at an end (or end portion) of the first main rod 120a, and a thickness of the first thick portion 120b may be greater than a thickness of the first main rod 120a. For example, as shown in FIG. 3, the first thick portion 120b may protrude toward the second transmitting coil 200 (e.g., in the negative Z-axis direction). Similarly, the second thick portion 220b may be at an end (or end portion) of the second main rod 220a, and a thickness of the second thick portion 220b may be greater than a thickness of the second main rod 220a. For example, the second thick portion 220b may protrude toward the first transmitting coil 100 (e.g., in the Z-axis direction). For example, the second thick portion 220b of the second transmitting coil 200 may protrude in a direction opposite to a protruding direction of the first thick portion 120b of the first transmitting coil 100. Because the first and second thick portions 120b and 220b of the first and second transmitting coils 100 and 200 may protrude toward the second and first transmitting coils 200 and 100, respectively, the distance along the Z-axis direction between the ends of the first rod 120 and the ends of the second rod 220 may be reduced or eliminated, and thus, the ends of the first and second rods 120 and 220 may be substantially coplanar.

The first wire 110 may be wound around the first rod 120 in any suitable configuration. The second wire 210 may be wound around the second rod 220 in any configuration that the first wire 110 may be wound around the first rod 120. In some embodiments, the first wire 110 is wound around the first main rod 120a and is not wound around the first thick portion 120b. The first wire 110 may be wound around substantially the entire length of the first main rod 120a. For example, the first wire 110 and the first main rod 120a may form a solenoid. In some embodiments, the first wire 110 is wound around two ends (or two end portions) of the first main rod 120a to form first and second sub-coils 110a and 110b at the two ends (or two end portions) of the first main rod 120a, and the first wire 110 exposes, and is not wound around, a portion (e.g., an exposed intermediate or central portion) of the first main rod 120a between the first and second sub-coils 110a and 110b. The exposed portion of the first main rod 120a may include a portion of the first main rod 120a corresponding to the area of overlap 300 between the first and second transmitting coils 100 and 200. When the first wire 110 is not wound around the first main rod 120a at the area of overlap 300, the thickness of the first transmitting coil 100 at the area of overlap 300 may be reduced.

The first sub-coil 110a may be electrically coupled (e.g., electrically connected) to the second sub-coil 110b in series or in parallel. When the first sub-coil 110a is electrically coupled (e.g., electrically connected) to the second sub-coil 110b in series, the first wire 110 may electrically couple (e.g., electrically connect) the first sub-coil 110a to the second sub-coil 110b by extending across the area of overlap 300 on the first main rod 120a and on a side of the first main rod 120a facing away from the second transmitting coil 200.

In some embodiments, the first sub-coil 110a is not electrically coupled (e.g., electrically connected) to the second sub-coil 110b, and the first and second sub-coils 110a and 110b are separately driven. In such embodiments, the first and second sub-coils 110a and 110b may be synchronously driven so that the magnetic fields generated by the first and second sub-coils coils 110a and 110b oscillate in phase.

The wireless power transfer device 10 may generate a magnetic field by driving the first AC current through the first wire 110 and/or driving the second AC current through the second wire 210. The first and second AC currents may be driven in phase (i.e., with about 0° phase difference between the first and second AC currents) or about 180° out of phase. A direction of the magnetic field generated by the wireless power transfer device 10 may be controlled by controlling (e.g., setting or changing) a first amplitude of the first AC current, a second amplitude of the second AC current, and a phase difference between the first and second AC currents (e.g., the wireless power transfer device 10 is configured to rotate the direction of the magnetic field by differentially driving the first and second transmitting coils 100 and 200). Accordingly, the direction of the magnetic field can be rotated by changing these parameters.

Figure 5A:
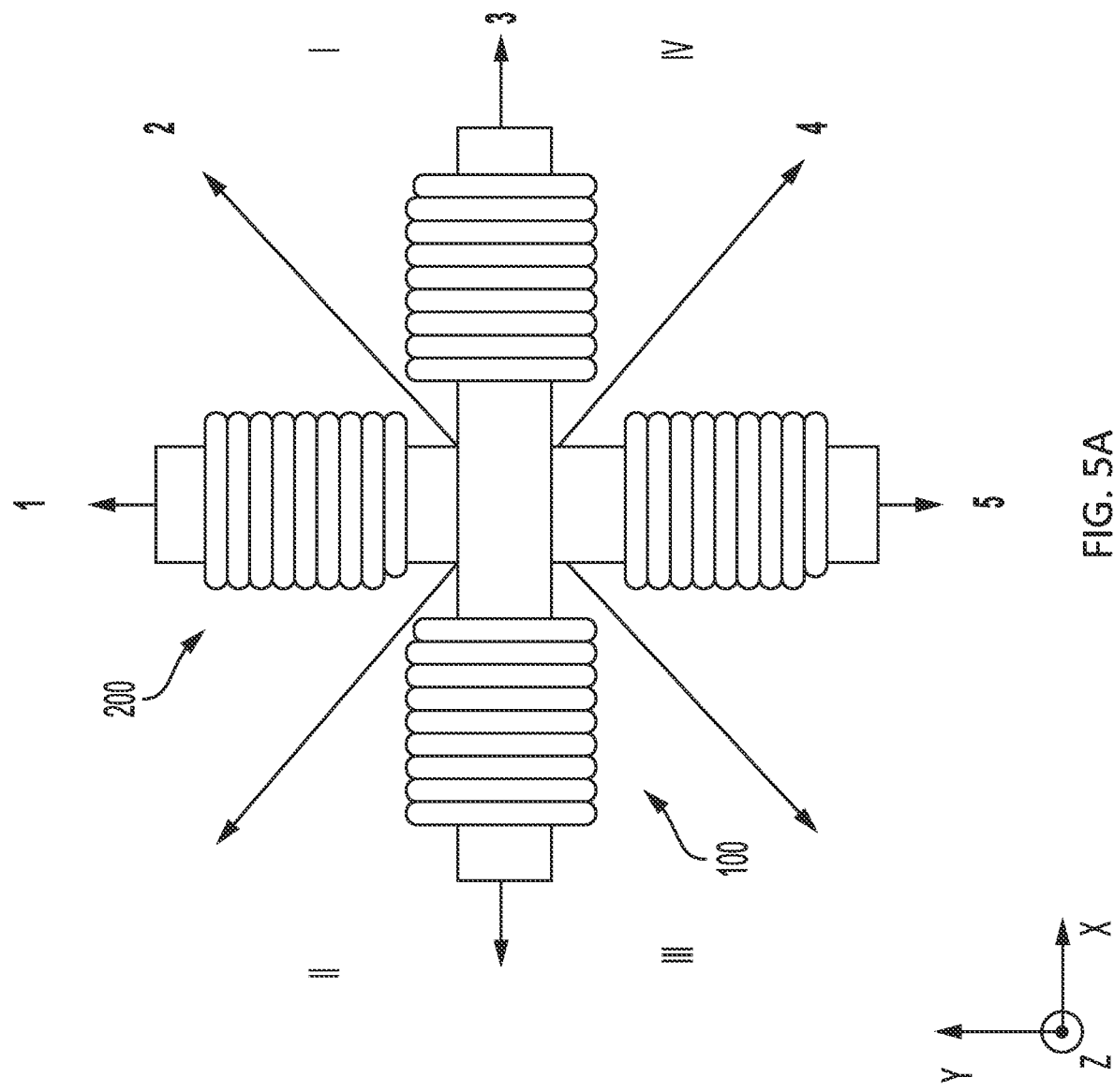
FIG. 5A shows a plan view of first and second transmitting coils of a wireless power transfer device according to some embodiments and the direction of a magnetic field generated by the first and second transmitting coils pursuant to five states in which the first and second transmitting coils may be driven.
Figure 5B:
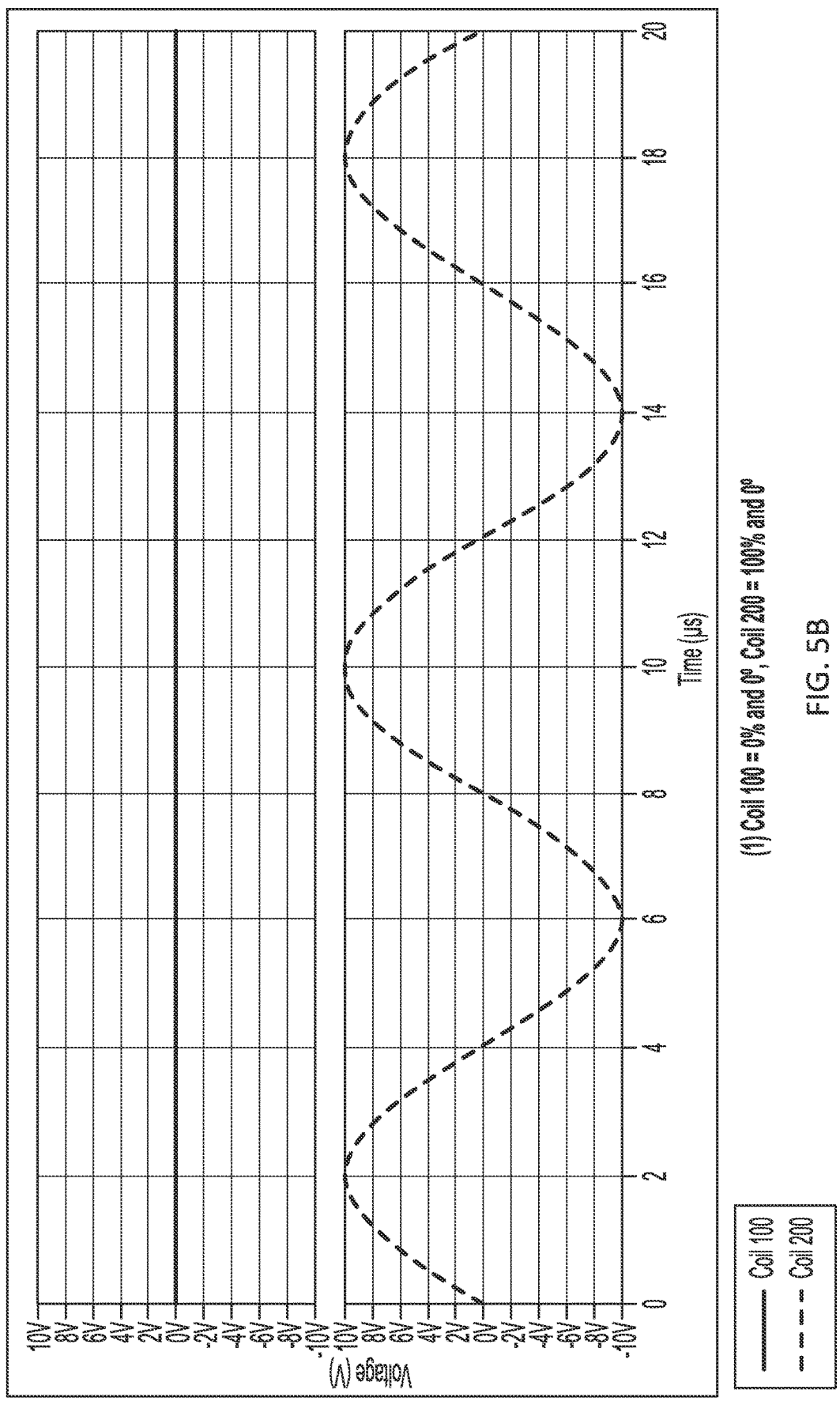

FIG. 5A shows how the direction of a magnetic field generated by the wireless power transfer device 10 can be rotated according to a non-limiting example. FIGS. 5B-5F show graphs of the voltages applied to the first and second transmitting coils 100 and 200 as a function of time for five states shown in FIG. 5A. The numerical values shown in the graphs of FIGS. 5B-5F represent non-limiting examples. Beginning with a first state (1) as shown in FIGS. 5A and 5B, the first amplitude of the first AC current of the first wire 110 is at 0, the second amplitude of the second AC of the second wire 210 current is at 10, and the direction of the magnetic field at a point above the area of overlap 300 may oscillate between the Y-axis direction and the negative Y-axis direction.

To rotate the magnetic field clockwise to a second position corresponding to a second state (2) as shown in FIGS. 5A and 5C, the first and second AC currents are driven in phase, the first amplitude is increased while the second amplitude is decreased until they are the same (each at an amplitude of 5), and the direction of the magnetic field at the point will oscillate between 45° between the X-axis direction and the Y-axis direction and 45° between the negative X-axis direction and the negative Y-axis direction.

Figure 5D:
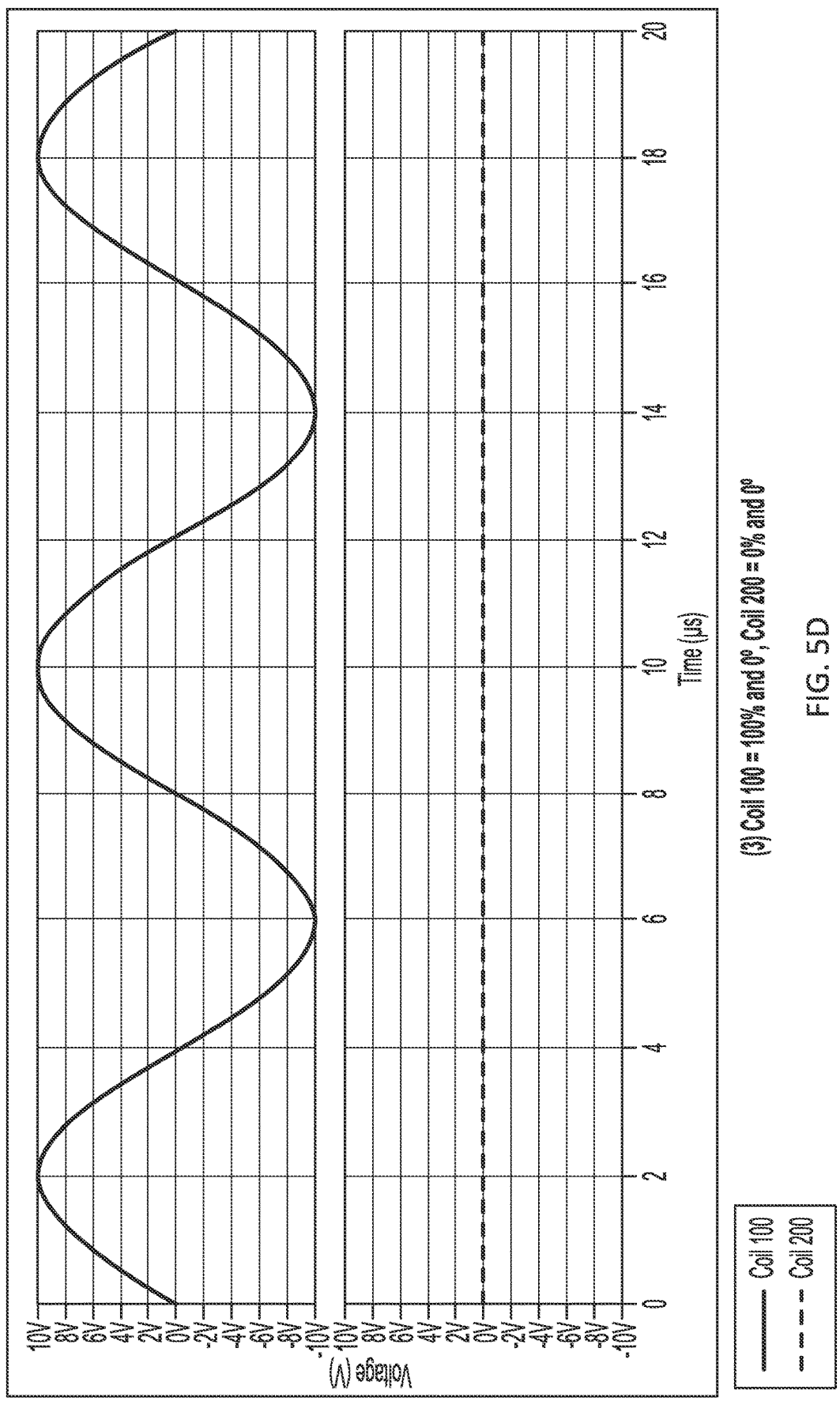

To rotate the magnetic field clockwise to a third position corresponding to a third state (3) as shown in FIGS. 5A and 5D, the first and second AC currents are driven in phase, the first amplitude is increased while the second amplitude is decreased until the first amplitude is at 10 and the second amplitude is at 0, and the direction of the magnetic field at the point will oscillate between the X-axis direction and the negative X-axis direction.

Figure 5E:
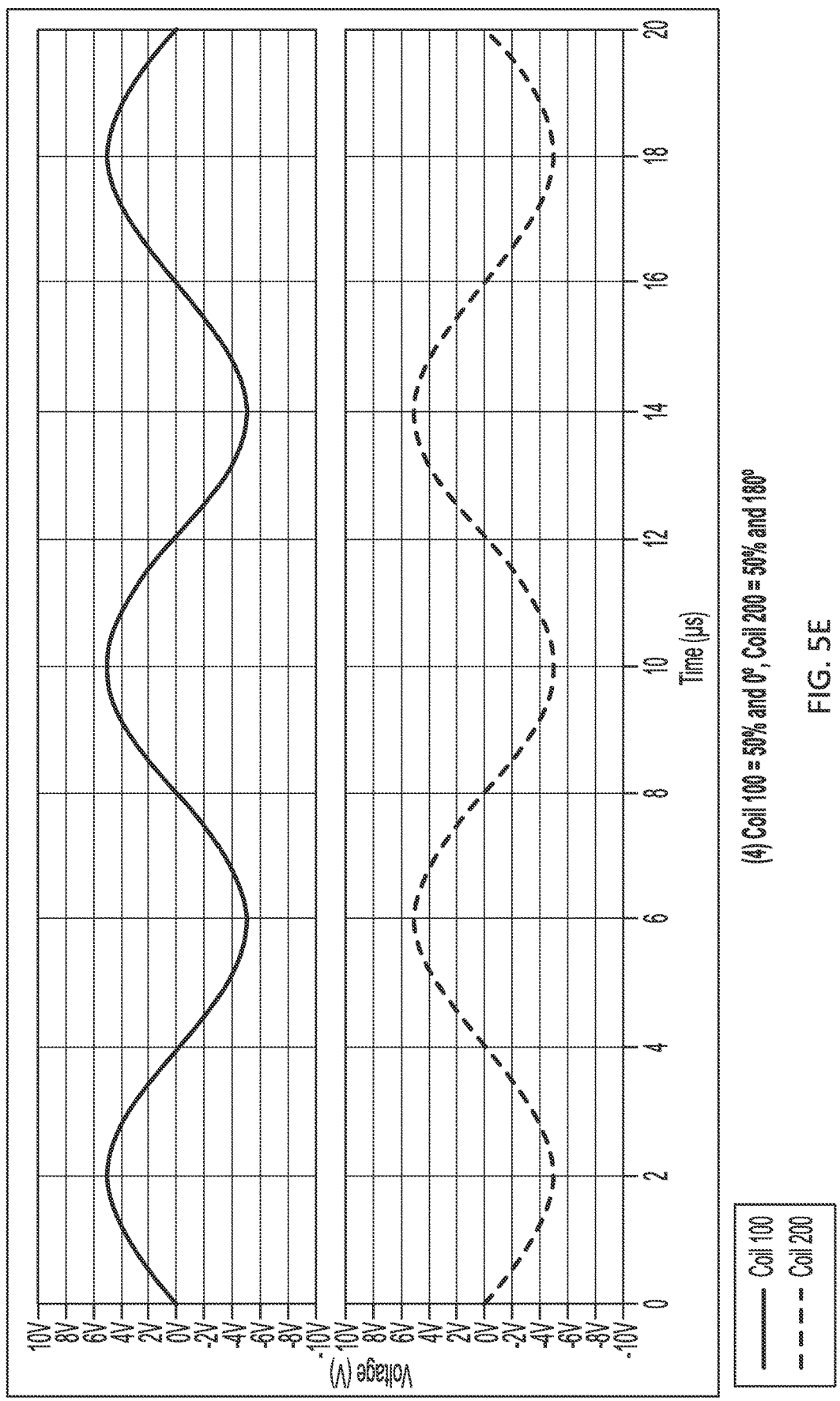

To rotate the magnetic field to a fourth position corresponding to a fourth state (4) as shown in FIGS. 5A and 5E, the first and second AC currents are driven 180° out of phase, the first amplitude is decreased while the second amplitude is increased until the first and second amplitudes are the same (each at 5), and the direction of the magnetic field at the point will oscillate between 45° between the X-axis direction and the negative Y-axis direction and 45° between the negative X-axis direction and the Y-axis direction.

Figure 5F:
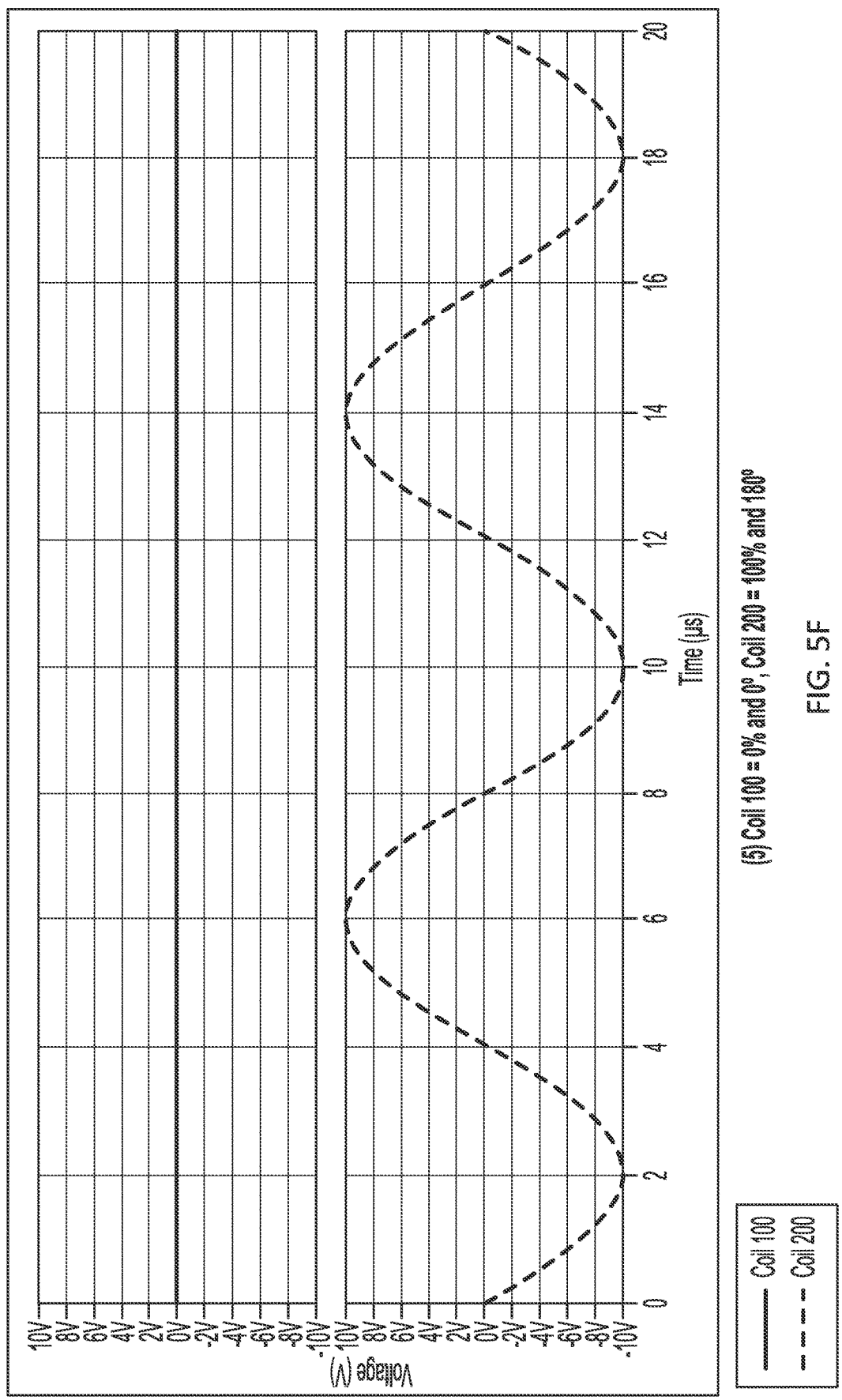

To rotate the magnetic field to a fifth position corresponding to a fifth state (5) as shown in FIGS. 5A and 5F, the first and second AC currents are driven 180° out of phase, the first amplitude is decreased while the second amplitude is increased until the first amplitude is at 0 and the second amplitude is at 10, and the direction of the magnetic field at the point may oscillate between the negative Y-axis direction and the Y-axis direction, similar to the first state (1). As used herein, the terms "first amplitude" and "second amplitude" refer to the peak amplitude.

Accordingly, the direction of the magnetic field at a point above the area of overlap 300 may be rotated to have any direction in the X-Y plane (any of quadrants I-IV of the X-Y plane in FIG. 5) by gradually adjusting the first amplitude of the first AC current and the second amplitude of the second AC current, and by shifting the first and second AC currents between being in-phase and being 180° out of phase. For example, when the first and second AC currents are in phase, the magnetic field at the point may have any direction in the first and third quadrants I and III of the X-Y plane by suitably setting the first and second amplitudes. Furthermore, when the first and second AC currents are 180° out of phase, the magnetic field at the point may have any direction in the second and fourth quadrants II and IV of the X-Y plane by suitably setting the first and second amplitudes.

Although a direction of the magnetic field generated by the wireless power transfer device 10 at a point above the area of overlap 300 has been described with respect to FIG.

5, it will be understood that the direction of the magnetic field at any point around the wireless power transfer device 10 may be controlled (e.g., rotated) as described above by controlling the first and second amplitudes and by controlling the phase difference between the first and second AC currents. The direction of the magnetic field at points away from regions above or below the area of overlap 300 may have a directional component along the Z-axis direction, whereas a direction of the magnetic field at regions above or below the area of overlap 300 may have substantially no Z-axis component.

The wireless power transfer device 10 may also include a power source, such as a rechargeable battery (e.g., a lithium-ion battery pack) or non-rechargeable battery (e.g., a replaceable battery), or the wireless power transfer device 10 may be configured to couple to (e.g., connect to), and be powered from, an external power source, such an electrical outlet. In some embodiments, the wireless power transfer device 10 includes a rechargeable battery and a power management system. A charger profile of the rechargeable battery may be set to not perform trickle charging, and the rechargeable battery may be allowed to charge to a set percentage of battery state of charge (SoC) of the rechargeable battery, for example, a percentage within a range of about 80% to about 90% of the SoC. The SoC of the rechargeable battery may refer to the maximum charge that the rechargeable battery is able to store.

Figure 6A:
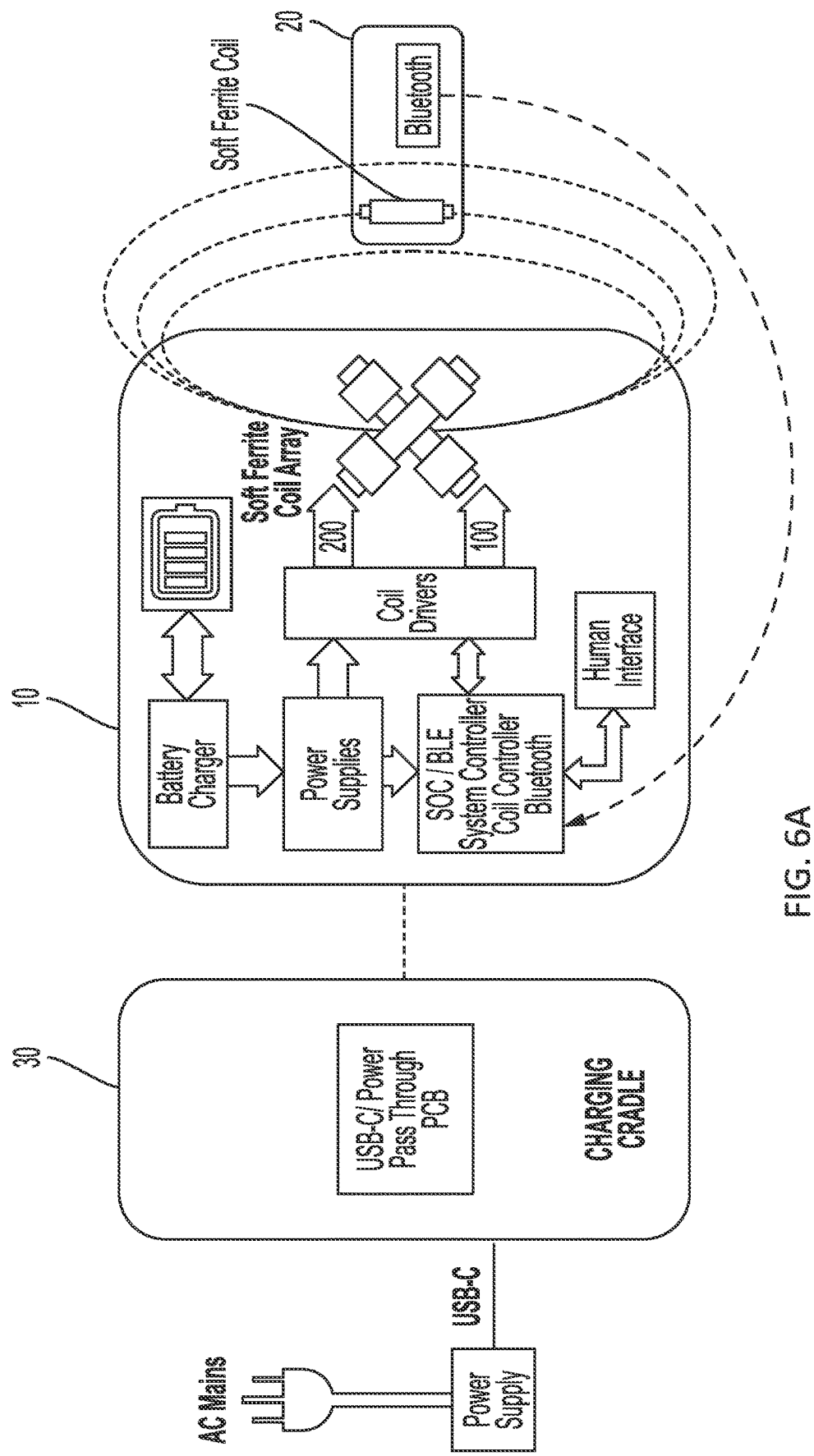
FIG. 6A shows a schematic view of a wireless power transfer system according to some embodiments.

Referring to FIG. 6A, which illustrates a wireless power transfer system according to some embodiments, the rechargeable battery of the wireless power transfer device 10 may be recharged through a power port or connector of the wireless power transfer device 10 that interfaces with a charging cradle 30. The wireless power transfer device 10 may be configured to be placed in or fixed to the charging cradle 30, and the wireless power transfer device 10 may be configured to detect the presence of a voltage at the power port or connector when it is placed in or fixed to the charging cradle 30. In some embodiments, the wireless power transfer device 10 is configured to allow the rechargeable battery to charge if the detected voltage value is equal to a set value or within a set range.

Referring again to FIG. 1, the driver 400 may include a first driver 410 to drive the first transmitting coil 100 and a second driver 420 to drive the second transmitting coil 200. In some embodiments, each of the first and second drivers 410 and 420 include a class D MOSFET bridge module, and the first and second drivers 410 and 420 may be respectively coupled (e.g., connected) in series to the first and second wires 110 and 210 through a capacitor to create a series resonant tank circuit, which may be tuned to 125 kHz. At the tuned frequency, the circuit may have the lowest impedance and highest quality factor.

Each of the first and second drivers 410 and 420 may receive an independent digital output signal from a digital port of the controller 600. Each of the digital output signals may be a driver signal, for example, a 125 kHz frequency, 50% duty cycle square wave. The two independent digital output signals may allow phase shifting between the first and second AC currents.

Each of the first and second drivers 410 and 420 may include an isolation current sensor respectively coupled (e.g., connected) in series with the first and second wires 110 and 210. The isolation current sensors may be configured to convert a current passing through the first and second drivers 410 and 420 into a proportional voltage which is rectified and signal conditioned. The signal may then be routed to an analog port of the controller 600 to be used as current feedback.

In some embodiments, the power modulation electronics 500 includes first power modulation electronics 510 and second power modulation electronics 520. The first and second power modulation electronics 510 and 520 may be respectively configured to provide power to the first and second drivers 410 and 420. The first and second power modulation electronics 510 and 520 may be independently controlled by respective analog output control signals received from the controller 600. In some embodiments, each of the first and second power modulation electronics 510 and 520 includes a single-ended primary-inductor converter (SEPIC) DC-to-DC converter that is configured to step-up or step-down a system bus voltage received at an input and to output the stepped-up or stepped-down voltage.

Each of the first and second power modulation electronics 510 and 520 may be configured to monitor their respective output voltages and provide overcurrent protection. In some embodiments, the first and second power modulation electronics 510 and 520 are configured to attenuate their respective output voltages, filter their output voltages via a capacitor, and couple (e.g., connect) their output voltages to respective analog inputs of the controller 600. For example, the first and second power modulation electronics 510 and 520 may be configured to provide their respective output voltages to the controller 600 as analog voltage feedback signals. The controller 600 may be configured to then provide respective digital signals to the first and second power modulation electronics 510 and 520 to enable or disable the first and second power modulation electronics 510 and 520 from providing power to the first and second drivers 410 and 420.

In some embodiments, the controller 600 is a Bluetooth™ low energy system on chip controller (BLE SOC). The controller 600 may be programmed via a JTAG or USB-C connector. In some embodiments, the controller 600 is configured to provide two analog output control signals to the first and second power modulation electronics 510 and 520, and the controller 600 is configured to receive two analog voltage feedback signals from the first and second power modulation electronics 510 and 520, which are utilized to monitor and adjust output power and to detect supply faults. Furthermore, the controller 600 may be configured to provide two digital output signals to the first and second drivers 410 and 420 to drive the first and second transmitting coils 100 and 200, and the controller 600 may be configured to provide two digital output signals to enable or disable the first and second power modulation electronics 510 and 520. The two digital output signals may be wave pulses having a frequency and duty cycle, such as 125 kHz and 50% duty cycle.

The controller 600 may be configured to control the power output from each of the first and second drivers 410 and 420 by controlling the respective bus voltages of the first and second power modulation electronics 510 and 520. The controller 600 may also be configured to control the phase difference between the first and second AC currents by changing a phase difference between the digital output signal pulse signals it provides to the first and second drivers 410 and 420. Accordingly, by controlling the power of the first and second AC currents and the phase difference between the first and second AC currents, the controller 600 may control the direction and magnitude of the magnetic fields generated by the first and second transmitting coils 100 and 200.

The wireless power transfer device 10 may be configured (e.g., via the controller 600) to communicate various suitable information to the user. Such information may include information about charging of the wireless power transfer device 10, information about charging of the electronic device 20, and various faults (e.g., defects, overheating, etc.). More details regarding what information the wireless power transfer device 10 may communicate to the user will be described below with reference to FIGS. 17-22. The wireless power transfer device 10 may communicate the information via any suitable means, for example, auditory signals, visual signals, and/or haptic feedback signals (e.g., vibrational signals). For example, referring to FIG. 6A, the charger 10 may include a human interface circuit that includes a piezoelectric based speaker, a vibration motor, and/or an LED light configured to communicate information.

Figure 7B:
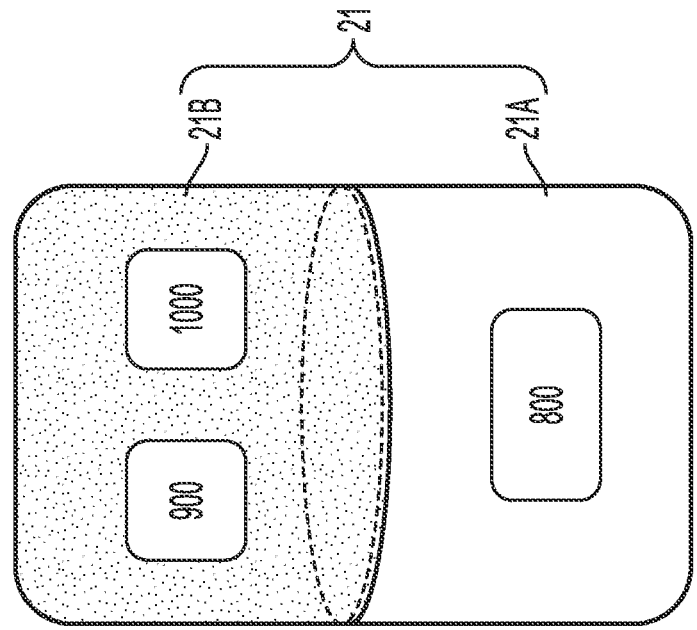
FIG. 7B shows a schematic view of an electronic device according to some embodiments.
Figure 7A:
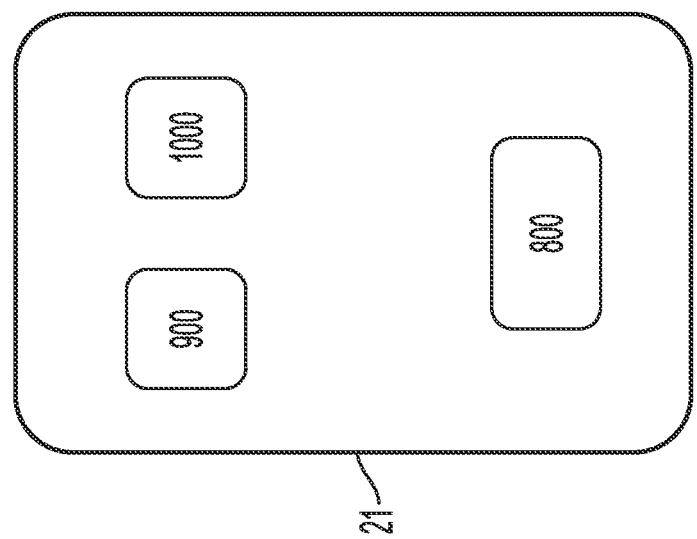
FIG. 7A shows a schematic view of an electronic device according to some embodiments.

The electronic device 20 may be an implantable device (e.g., a device that is configured to be inserted in vivo). In some embodiments where the electronic device 20 is an implantable medical device, the electronic device 20 may include a casing 21 that encases the components of the electronic device 20. In some embodiments, as shown in FIG. 7A, the entire casing 21 may include a metallic material. In some other embodiments, as shown in FIG. 7B, a first portion 21A of the casing 21 may include a ceramic material and a second portion of 21B of the casing 21 may include a metallic material. The first portion 21A may cover the receiver coil 800, and the second portion 21B may cover the other components of the electronic device 20 (e.g., the detector 900 and the transmitter 1000). The size and configuration of the first and second portions 21A and 21B may depend, for example, on the sizes, shapes, and relative positions of the receiver coil 800 and the other components of the electronic device 20. In some embodiments, a portion of the casing 21 may include a plastic, an epoxy, and/or a polymer material.

The electronic device 20 is not limited to implantable devices or medical devices, and the electronic device 20 may be any suitable device configured to receive power and/or generate an electrical current via electromagnetic induction. In some embodiments, the electronic device 20 may be configured to store energy of the current generated in the receiver coil 800, for example, in a capacitor. However, the present disclosure is not limited thereto, and the electronic device 20 may be configured in some embodiments to utilize the current without storing the energy of the current. For example, energy of the current generated in the receiver coil 800 may be utilized to drive or power other components in the electronic device 20.

When the electronic device 20 is in the proximity of the wireless power transfer device 10, and the wireless power transfer device 10 generates an oscillating magnetic field, a current may be generated in the receiver coil 800 by electromagnetic induction via the oscillating magnetic field. The receiver coil 800 may be, for example, a solenoid with a ferrimagnetic (e.g., soft ferrite) core.

The detector 900 may be electrically coupled (e.g., electrically connected) to the receiver coil 800 and configured to detect information about the current (e.g., the power or amplitude of the current) generated in the receiver coil 800.

The transmitter 1000 may transmit the information detected by the detector 900 to the receiver 700 of the wireless power transfer device 10, but the present disclosure is not limited thereto. The transmitter 1000 may be configured to transmit the information to any suitable receiver outside of the electronic device 20 that is able to receive the information transmitted by the transmitter 1000. In some embodiments, the transmitter 1000 transmits information wirelessly, for example, via Bluetooth™ low energy (BLE).

Aligning the orientation of magnetic field at the receiver coil 800 with the receiver coil 800 increases the efficiency at which the wireless power transfer device 10 transfers power to the electronic device 20 compared to otherwise comparable wireless power transfer devices and receiver coils in which the magnetic field is misaligned. Accordingly, the wireless power transfer device 10 may rotate the magnetic field in order to align (e.g., optimally align) the magnetic field with the receiver coil 800.

A feedback system that monitors (e.g., directly or indirectly monitors) the relative direction of the magnetic field at the receiver coil 800 may be utilized to align (or to enable an operator to align) the magnetic field with the receiver coil 800. The feedback system may allow the wireless power transfer device 10 to automatically align the magnetic field with, or to create a magnetic field that is aligned with, the receiver coil 800 at the receiver coil 800 without requiring a user to manually adjust the position and/or orientation of the wireless power transfer device 10 after placing the wireless power transfer device 10 in proximity with the electronic device 20. Two example feedback systems will now be described in more detail.

In a first feedback system, the wireless power transfer device 10 generates an initial magnetic field and rotates the initial magnetic field (e.g., in the manner described above with reference to FIG. 5). As the initial magnetic field is rotated, the detector 900 detects information (e.g., power or amplitude) of the current generated in the receiver coil 800. The power received in the receiver coil 800 (e.g., the power of the current generated in the receiver coil 800) may correlate with how aligned the initial magnetic field is with the receiver coil 800. Accordingly, a maximum detected power may correspond to alignment (e.g., optimal alignment) between the initial magnetic field and the receiver coil 800. The maximum detected power also indicates what values of the first amplitude, the second amplitude, and the relative phase between the first and second AC currents generate a magnetic field that will be aligned with the receiver coil 800. After this information is obtained, the wireless power transfer device 10 may generate a magnetic field aligned with the receiver coil 800 to charge (or drive) the electronic device 20.

In a second feedback system, load modulation may be utilized. Load modulation is described in Griffith, U.S. Pat. No. 9,962,085 and Finkenzeller, "Battery Powered Tags for ISO/IEC 14443, Actively Emulating Load Modulation," *RFID SysTech* 2011 *7th European Workshop on Smart Objects: Systems, Technologies and Applications* (2011), the entire content of each of which is incorporated herein by reference.

In the second feedback system, the wireless power transfer device 10 may generate an initial magnetic field and rotate the initial magnetic field (e.g., in the manner described above with reference to FIG. 5). The electronic device 20 may include a modulation resistance coupled (e.g., connected in parallel) to the receiver coil 800, and the modulation resistance can be turned on and off to cause the receiver coil 800 to transmit a signal back to the wireless power transfer device 10 while the electronic device 20 receives power from the wireless power transfer device 10. Information in the signal may be controlled, for example, by the clock rate at which the modulation resistance is turned on and off. The signal may include information about how aligned (i.e., the degree or extent of alignment) the initial magnetic field is with the receiver coil 800. The signal may be measured by a demodulator in the wireless power transfer device 10 that is coupled to one or both of the first and second transmitting coils 100 and 200. The information in the signal may be utilized to determine what values of the first amplitude, the second amplitude, and the relative phase between the first and second AC currents generate a magnetic field that will be aligned with the receiver coil 800. After this information is obtained, the wireless power transfer device 10 may generate a magnetic field that is aligned with the receiver coil 800 to charge (or drive) the electronic device 20.

In some embodiments, the values of the first amplitude, the second amplitude, and the phase difference between the first and second AC currents that can generate a magnetic field that is aligned with the receiver coil 800 may be determined after the wireless power transfer device 10 rotates the magnetic field through a range of degrees (e.g., the wireless power transfer device 10 sweeps the magnetic field through a range of orientations), for example, a full 180° sweep (360° when taking into account the oscillating nature of the magnetic field), but the present disclosure is not limited thereto. For example, information regarding how aligned the initial magnetic field is with the receiver coil 800 may be continuously monitored, and the wireless power transfer device 10 (e.g., the controller 600 of the wireless power transfer device 10) may stop the rotation when alignment (e.g., optimal alignment) between the initial magnetic field and the receiver coil 800 has been detected. The wireless power transfer device 10 may then charge (or drive) the electronic device 20.

Figure 6B:
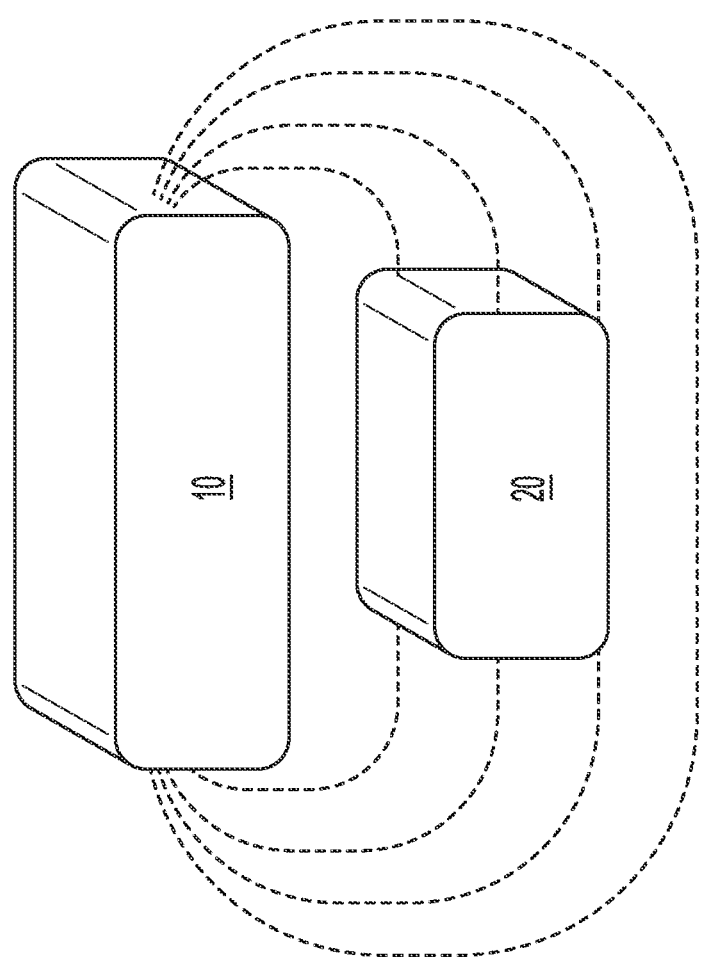
FIG. 6B shows a schematic side view of the wireless power transfer system of FIG. 6A with the wireless power transfer device above the electronic device.
Figure 6C:
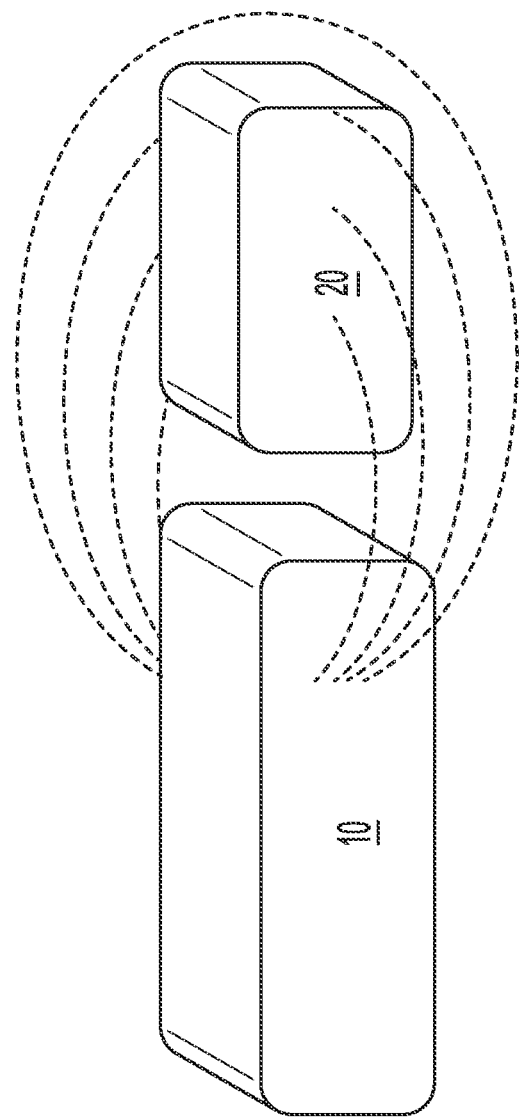
FIG. 6C shows a schematic side view of the wireless power transfer system of FIG. 6A with the electronic device at the side of the wireless power transfer device.

The wireless power transfer device 10 may be configured to transfer power to the electronic device 20 regardless of where the electronic device 20 is positioned relative to the wireless power transfer device 10. For example, FIGS. 6B and 6C show schematic side views of the wireless power transfer device 10 and electronic device 20 of the wireless power transfer system of FIG. 6A with the electronic device 20 in two different positions relative to the wireless power transfer device 10. That is, FIGS. 6B and 6C show side views of a plane substantially defined by the first and second transmitting coils 100 and 200. FIG. 6B shows a non-limiting example where the wireless power transfer device 10 transfers power to the electronic device 20 while being positioned above (e.g., while an area of overlap between the first and second transmitting coils 100 and 200 is positioned above) the electronic device 20. FIG. 6C shows a non-limiting example where the wireless power transfer device 10 transfers power to the electronic device while the electronic device 20 is positioned at the side of the wireless power transfer device 10 (e.g., at the side of the first and second transmitting coils 100 and 200).

Figure 8:
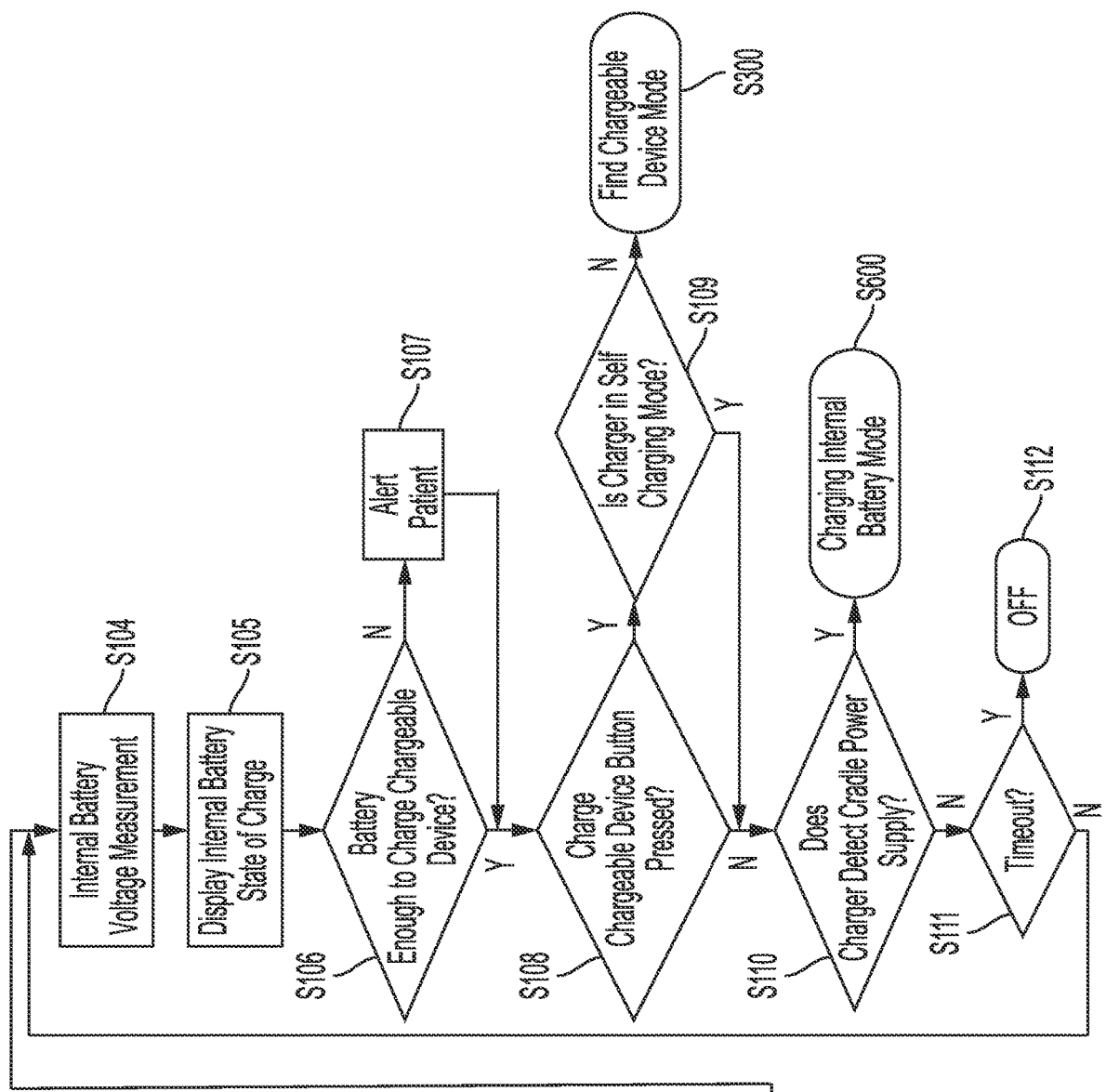
FIG. 8 shows a method flow chart for an initialization mode according to some embodiments.
Figure 8:
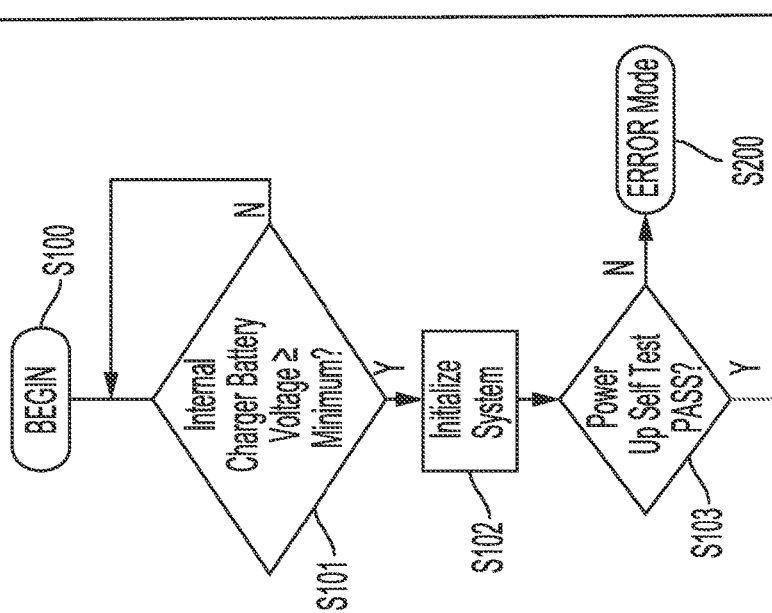
Figure 9:
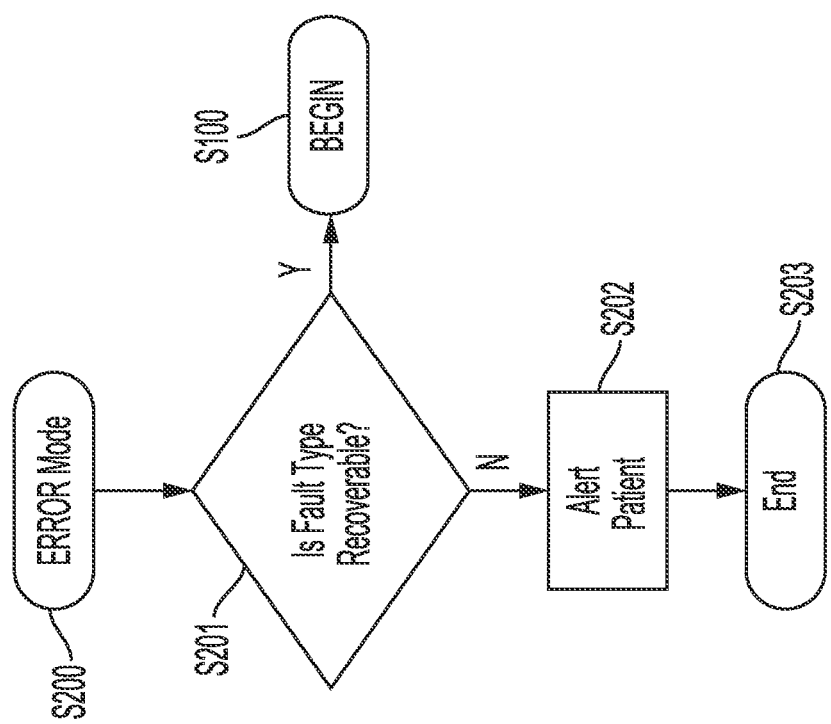
FIG. 9 shows a method flow chart for an error mode according to some embodiments.
Figure 10:
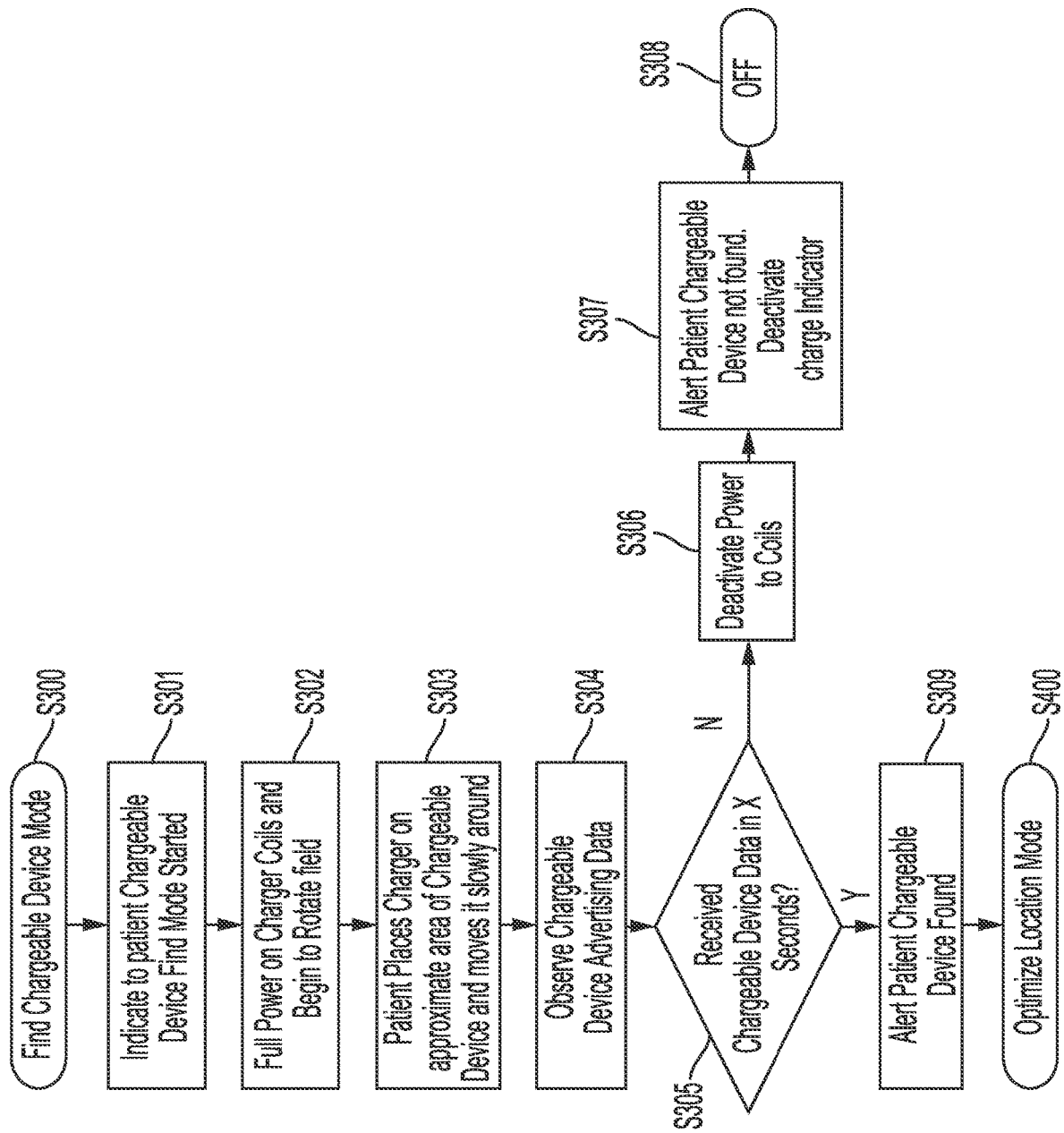
FIG. 10 shows a method flow chart for a find electronic device mode according to some embodiments.
Figure 11:
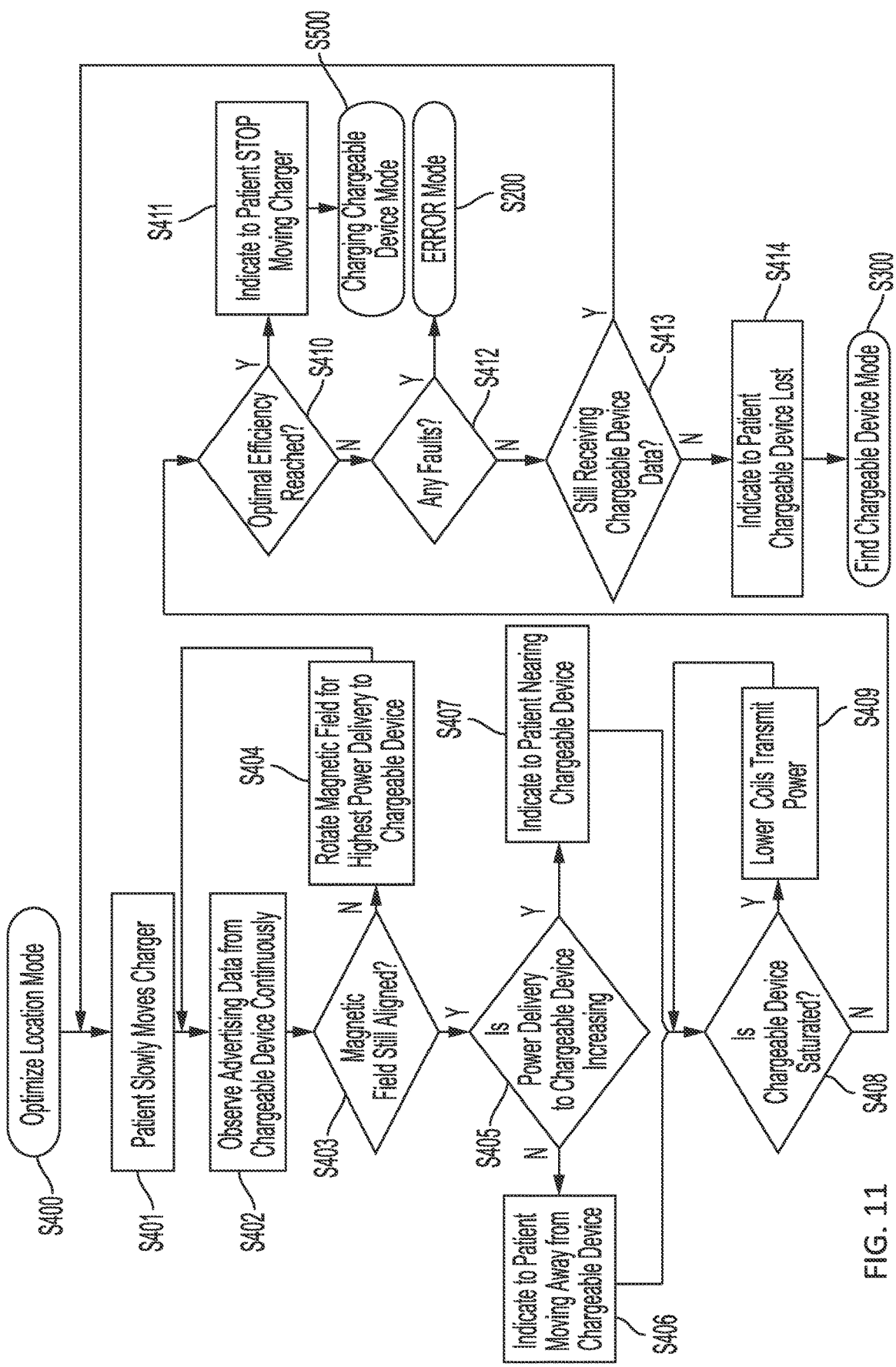
FIG. 11 shows a method flow chart for an optimize location mode according to some embodiments.
Figure 12:
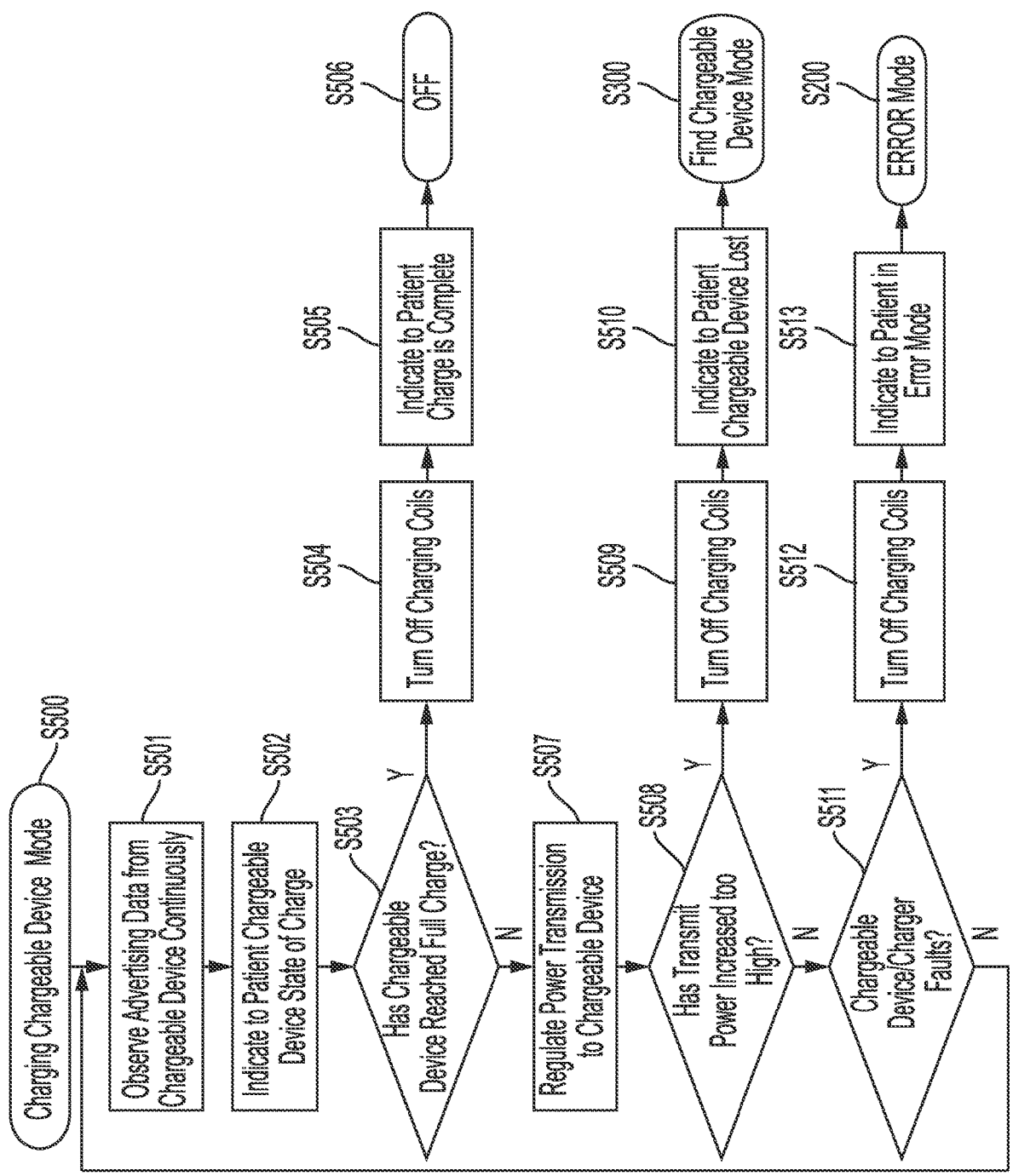
FIG. 12 shows a method flow chart for an electronic device charging mode according to some embodiments.
Figure 13:
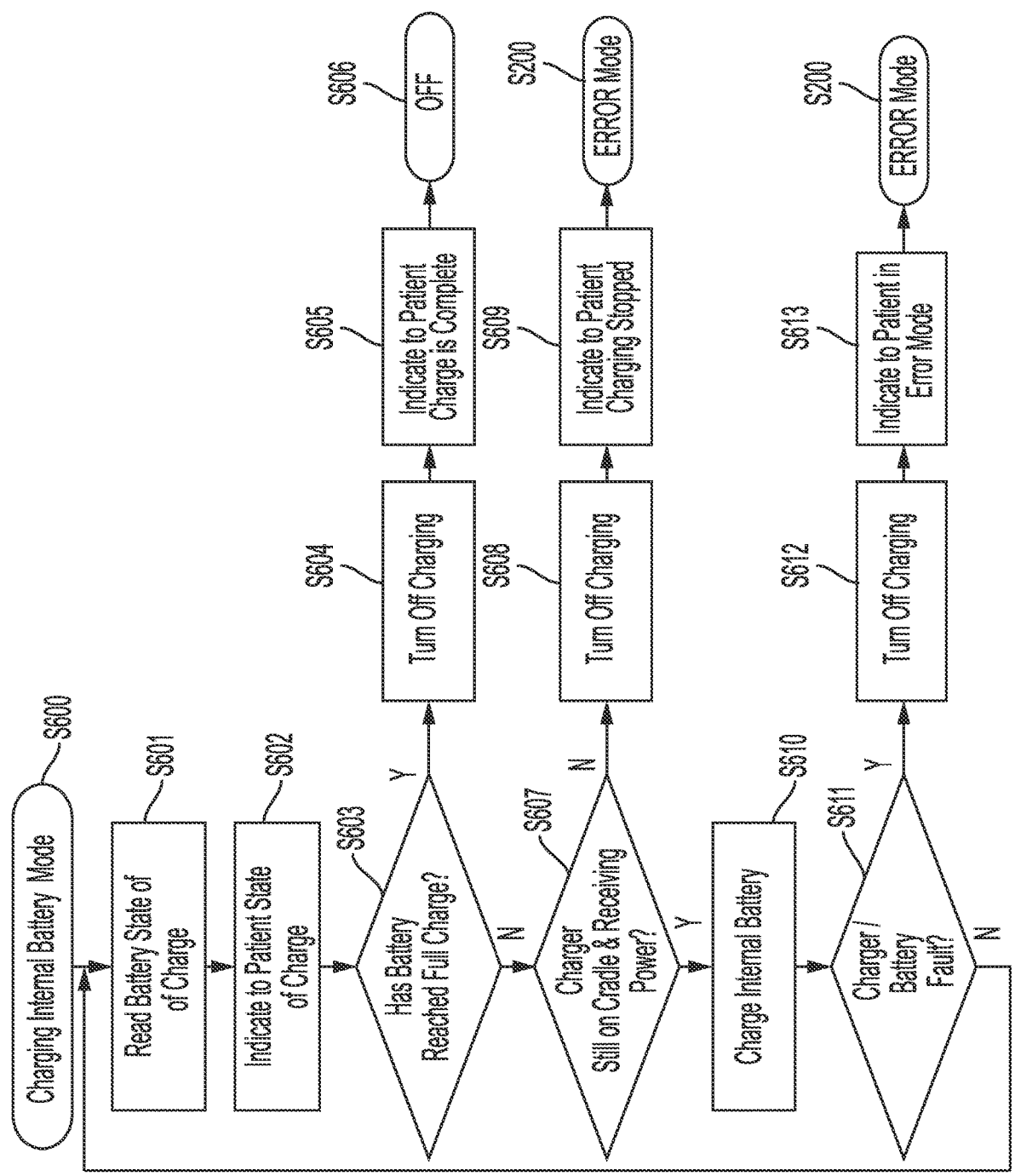
FIG. 13 shows a method flow chart for a wireless power transfer device charging mode according to some embodiments.

Various modes of operating a wireless power transfer system will now be described in more detail with reference to FIGS. 8-13. FIG. 8 illustrates an initialization mode; FIG. 9 illustrates an error mode; FIG. 10 illustrates a find the electronic device mode; FIG. 11 illustrates an optimize location mode; FIG. 12 illustrates an electronic device charging mode; and FIG. 13 illustrates a wireless power transfer device charging mode.

Referring to FIG. 8, an Initialization mode may begin at stage S100. The initialization mode may begin, for example, when the wireless power transfer device 10 is placed in the charging cradle 30, when a charge button is pressed, or when the wireless power transfer device 10 is trying to recover from a recoverable error. The charge button may be a button on the wireless power transfer device 10 that allows a user to initialize the wireless power transfer device 10 for charging the electronic device 20.

At stage S101, the wireless power transfer device 10 may determine whether a voltage of an internal battery (e.g., a rechargeable battery) of the wireless power transfer device 10 is greater than or equal to a minimum voltage. If the voltage of the internal battery is less than the minimum voltage, then the wireless power transfer device 10 may repeat stage S101. However, if the voltage of the internal battery is greater than or equal to the minimum voltage, the wireless power transfer device 10 may initialize the system of the wireless power transfer device 10 at stage S102.

After the wireless power transfer device 10 is initialized at stage S102, the wireless power transfer device 10 may perform a power up self-test at stage S103. For example, the wireless power transfer device 10 may test for internal faults (e.g., defects) or errors during stage S103, and the wireless power transfer device 10 may begin an error mode at stage S200 if the wireless power transfer device 10 detects an error such that the power up self-test fails. However, if at stage S103 the power up self-test is passed, the wireless power transfer device 10 may measure a voltage of the internal battery at stage S104 and communicate to the user the SoC of the internal battery at stage S105.

At stage S106, the wireless power transfer device 10 may determine whether the SoC of the internal battery is sufficient to charge (or drive) the electronic device 20. If the SoC of the internal battery is insufficiently low, the wireless power transfer device 10 may alert the user at S107 and proceed to stage S108. However, if at stage S106 the SoC is determined to be sufficient, the wireless power transfer device 10 may determine whether the charge button has been pressed at stage S108.

If the charge button has been pressed, the wireless power transfer device 10 may determine whether it is in a self-charging mode at stage S109. If the wireless power transfer device 10 is not in the self-charging mode, then the wireless power transfer device 10 may begin the find electronic device mode at stage S300. However, if at stage S109 the wireless power transfer device 10 is in the self-charging mode, the wireless power transfer device 10 may proceed to stage S110. Furthermore, if at stage S108 it is determined that the charge button has not been pressed, the wireless power transfer device 10 may detect whether a power supply from the charging cradle 30 is available.

If the wireless power transfer device 10 detects the power supply from the charger cradle 30, the wireless power transfer device 10 may begin the wireless power transfer device charging mode at stage S600. However, if at stage S110 the wireless power transfer device 10 does not detect the power supply from the charger cradle 30, the wireless power transfer device 10 may determine at stage S111 whether a set (e.g., predetermined) amount of time has passed since a previous stage, for example, stage S102 or stage S103.

If the wireless power transfer device 10 determines that the set amount of time has not elapsed, then the wireless power transfer device 10 may proceed to stage S104. However, if the set amount of time has elapsed, then the wireless power transfer device 10 may turn off at stage S112.

Referring to FIG. 9, after the error mode begins at stage S200, the wireless power transfer device 10 may determine at stage S201 whether it is able to recover from (e.g., resolve or remedy) the fault. If the wireless power transfer device 10 is able to recover from the fault, the wireless power transfer device 10 may begin the initialization mode at stage S100.

However, if the wireless power transfer device 10 is unable to recover from the fault, the wireless power transfer device 10 may alert the user at stage S202 that the wireless power transfer device 10 is unable to recover. The wireless power transfer device 10 may then end the error mode at stage S203. In some embodiments, the wireless power transfer device 10 may turn off at stage S203.

Referring to FIG. 10, after the find electronic device mode begins at stage S300, the wireless power transfer device 10 may communicate to the user that the find electronic device mode has started. The wireless power transfer device 10 may drive the first and second transmitting coils 100 and 200 to generate and rotate an initial magnetic field at stage S302. At stage S303, the wireless power transfer device 10 may be placed at an initial position in approximate or estimated proximity to the electronic device 20, and the wireless power transfer device 10 may be moved slowly around the initial position. At stage S304, the wireless power transfer device 10 may communicate information to the user regarding whether the electronic device 20 has been located, for example, by receiving a signal from the electronic device 20, while the wireless power transfer device 10 is moved around the initial position.

The wireless power transfer device 10 may determine at stage S305 whether the electronic device 20 has been located within a set amount of time, for example, from a previous stage such as S303. If the electronic device 20 has not been located when the set amount of time elapses, the wireless power transfer device 10 may stop driving the first and second transmitting coils 100 and 200 to terminate the initial magnetic field at stage S306. The wireless power transfer device 10 may then communicate to the user that the electronic device 20 was not found at stage S307, and the wireless power transfer device 10 may turn off at stage S308. However, if at stage S305 the wireless power transfer device 10 determines within the set amount of time that the electronic device 20 has been found, then the wireless power transfer device 10 may communicate to the user that the electronic device 20 has been found at stage S309. The wireless power transfer device 10 may then begin an optimize location mode at stage S400.

Referring to FIG. 11, after the optimize location mode begins at stage S400 and at stage S401, the wireless power transfer device 10 may be slowly moved, for example, from a second position where the wireless power transfer device 10 was located when the electronic device 20 was found. The wireless power transfer device 10 may continuously communicate information to the user at stage S402 while the wireless power transfer device 10 is being moved. The information communicated at stage S402 may include whether the initial magnetic field is aligned with the receiver coil 800 and whether power delivered to the electronic device 20 is increasing or decreasing. The wireless power transfer device 10 may determine whether the initial magnetic field is aligned with the receiver coil 800 by utilizing a feedback system as described above.

At stage S403, the wireless power transfer device 10 may determine whether the initial magnetic field is aligned with the receiver coil 800. If the initial magnetic field is not aligned, the wireless power transfer device 10 may rotate the initial magnetic field as needed (e.g., by utilizing a feedback system as described above) at stage S404 to automatically align the initial magnetic field with the receiver coil 800. However, if at stage S403 the wireless power transfer device 10 determines that the initial magnetic field is aligned with the receiver coil 800, then the wireless power transfer device 10 may determine at stage S405 whether power delivered to the electronic device 20 is increasing as the wireless power transfer device 10 is moved. The wireless power transfer device 10 may then communicate to the user whether the wireless power transfer device 10 is being moved away from the electronic device 20 (stage S406) or toward the electronic device 20 (stage S407).

At stage S408, the wireless power transfer device 10 may determine whether the receiver coil 800 is saturated. Saturation of the receiver coil 800 may occur when an increase in magnitude of the initial magnetic field at the receiver coil 800 does not significantly increase the magnetization of the core material (e.g., ferrimagnetic material) of the receiver coil 800. If it is determined that the receiver coil 800 is saturated, the first and second amplitudes of the first and second currents used to generate the initial magnetic field may be reduced at stage S409, and the wireless power transfer device 10 may again determine whether the receiver coil 800 is saturated at stage S408. However, if at stage S408 it is determined that the receiver coil 800 is not saturated, the wireless power transfer device 10 may determine whether the wireless power transfer device 10 is at an optimal position and/or orientation at stage S410. The optimal position and/or orientation may correspond to a position and/or orientation of the wireless power transfer device 10 that results in a maximum power received in the receiver coil at set amplitudes of the first and second AC currents that do not saturate the receiver coil 800.

If it is determined that the wireless power transfer device 10 is at an optimal position and/or orientation, the wireless power transfer device 10 may communicate to the user to stop moving the wireless power transfer device 10 at stage S411, and the wireless power transfer device 10 may begin the electronic device charging mode at stage S500. However, if at stage S410 it is determined that the wireless power transfer device 10 is not at an optimal position and/or orientation, the wireless power transfer device 10 may conduct a test to detect faults at stage S412. If a fault is detected, the wireless power transfer device 10 may begin the error mode at stage S200. However, if no faults are detected, the wireless power transfer device 10 may determine whether information from the electronic device 20 is still being received at stage S413.

If information from the electronic device 20 is still being received, the user may continue to move the wireless power transfer device 10 at stage S401. For example, the wireless power transfer device 10 may prompt the user to continue to move the wireless power transfer device 10. However, if at stage S413 the wireless power transfer device 10 determines that information is not being received from the electronic device 20, the wireless power transfer device 10 may communicate to the user at stage S414 that the electronic device 20 has been lost, and the wireless power transfer device 10 may begin the find electronic device mode at stage S300.

Referring to FIG. 12, after the electronic device charging mode begins at stage S500, information from the electronic device 20 may be continuously received and monitored at stage S501, and the wireless power transfer device 10 may communicate information about the electronic device 20 (e.g., SoC of a battery or of an energy storage in the electronic device 20) to the user at stage S502.

At stage S503, the wireless power transfer device 10 may determine whether the electronic device 20 has reached a set SoC of the electronic device 20. For example, the wireless power transfer device 10 may determine whether the electronic device 20 has reached a fully charged state. If the electronic device 20 has reached the set SoC, the wireless power transfer device 10 may stop driving the first and second transmitting coils 100 and 200 at stage S504 to terminate the magnetic field generated by the wireless power transfer device 10. The wireless power transfer device 10 may then communicate to the user that the charge is complete at stage S505 before turning off at stage S506.

However, if at stage S503 the wireless power transfer device 10 determines that the set SoC of the electronic device 20 has not been reached, it may regulate power transmission to the electronic device 20 at stage S507. For example, the wireless power transfer device 10 may change the amplitudes of the first and second AC currents to reduce or increase the power provided to the electronic device 20.

At stage S508, the wireless power transfer device 10 may determine whether transmission power is at or above a set or predetermined threshold. If the transmission power is at or above the set or predetermined threshold, the wireless power transfer device 10 may turn off the first and second transmitting coils 100 and 200 at stage S509 to terminate the magnetic field. The wireless power transfer device 10 may then communicate to the user that the electronic device 20 has been lost at stage S510 and begin the find electronic device mode at stage S300.

However, if at stage S508 the wireless power transfer device 10 determines that the transmission power is below the set or predetermined threshold, then the wireless power transfer device 10 may determine whether any faults have occurred in the wireless power transfer device 10 and/or in the electronic device 20 at stage S511. If a fault is detected, the wireless power transfer device 10 may turn off the first and second transmitting coils 100 and 200 at stage S512. The wireless power transfer device 10 may then communicate to the user that a fault has been found and begin the error mode at stage S200.

However, if at stage S511 the wireless power transfer device 10 does not detect any faults, the wireless power transfer device 10 may proceed to stage S501 and continue to receive and monitor information received from the electronic device 20.

Referring to FIG. 13, the wireless power transfer device 10 may begin charging an internal battery via a power supply provided by the charging cradle 30 at stage S600 of the wireless power transfer device charging mode. The wireless power transfer device 10 may determine a SoC of the internal battery at stage S601 and communicate the SoC to the user at stage S602. At stage S603, the wireless power transfer device 10 may determine whether a set SoC of the internal battery has been reached. For example, the wireless power transfer device 10 may determine whether the internal battery has been fully charged.

If the wireless power transfer device 10 determines that the set SoC of the internal battery has been reached, the wireless power transfer device 10 may stop charging the internal battery at stage S604, communicate to the user that the charging process is complete at stage S605, and turn off at stage S606.

However, if at stage S603 the wireless power transfer device 10 determines that the internal battery has not reached the set SoC, the wireless power transfer device 10 may determine whether the wireless power transfer device 10 is still coupled to (e.g., on or in) the charger cradle 30 and receiving power from the charger cradle 30. If the wireless power transfer device 10 is not coupled to the charger cradle 30 or not receiving power from the charger cradle 30, the wireless power transfer device 10 may stop charging the internal battery at stage S608, communicate to the user that the charging process has stopped at stage S609, and begin the error mode at stage S200.

However, if at stage S607 the wireless power transfer device 10 determines that the wireless power transfer device 10 is coupled to the charger cradle 30 and is receiving power from the charger cradle 30, the wireless power transfer device 10 may continue to charge the internal battery at stage S610. At stage S611, the wireless power transfer device 10 may determine whether faults have occurred in the wireless power transfer device 10 and/or in the internal battery at stage S611. If a fault is detected, the wireless power transfer device 10 may stop the charging process at stage S612, communicate to the client that the charging process has stopped at stage S613, and begin the error mode at stage S200.

However, if at stage S611 the wireless power transfer device 10 does not detect any faults, the wireless power transfer device 10 may proceed to stage S601 to determine the SoC of the internal battery.

Although some embodiments of the present disclosure have disclosed herein, the present disclosure is not limited thereto, and the scope of the present disclosure is defined by the appended claims and equivalents thereof.

What is claimed is:

1. A wireless power transfer system comprising a wireless power transfer device, the wireless power transfer device comprising:
   a first transmitting coil oriented along a first axis;
   a second transmitting coil on the first transmitting coil and oriented along a second axis different from the first axis;
   a nonmagnetic material magnetically decoupling the first transmitting coil from the second transmitting coil in an area of overlap between the first and second transmitting cons; and
   a driver configured to provide a first current to the first transmitting coil and a second current to the second transmitting coil to generate a magnetic field,
   wherein the driver is configured to differentially drive the first and second transmitting coils, by independently controlling amplitudes of the first and second currents, to control a direction of the magnetic field,
   wherein the first transmitting coil comprises a first rod and a first wire wound around the first rod,
   wherein the second transmitting coil comprises a second rod and a second wire wound around the second rod,
   wherein the first wire comprises a first sub-con at one end of the first rod and a second sub-coil at another end of the first rod and s aced a art from the first sub-coil, and
   wherein the second wire comprises a third sub-coil at one end of the second rod and a fourth sub-con at another end of the second rod and spaced apart from the third sub-coil.

2. The wireless power transfer system of claim 1, wherein:
   the first rod comprises a magnetic material, and
   the second rod comprises a magnetic material.

3. The wireless power transfer system of claim 2, wherein the magnetic material of the first rod comprises a ferrimagnetic material, the magnetic material of the second rod comprises a ferrimagnetic material, and the nonmagnetic material comprises air.

4. The wireless power transfer system of claim 1, wherein the first sub coil, the second sub-coil, the third sub-coil, and the fourth sub-con are substantially coplanar.

5. The wireless power transfer system of claim 1, wherein the first wire exposes the first rod at the area of overlap and the second wire exposes the second rod at the area of overlap.

6. The wireless power transfer system of claim 1, wherein the first axis is perpendicular to the second axis.

7. The wireless power transfer system of claim 1, wherein the wireless power transfer device further comprises:
   a controller configured to control the first current and the second current provided by the driver.

8. The wireless power transfer system of claim 7, further comprising an electronic device comprising a receiver coil.

9. The wireless power transfer system of claim 8, wherein the electronic device is an implantable medical device.

10. The wireless power transfer system of claim 9, wherein the implantable medical device comprises a casing, a portion of the casing around the receiver coil comprising a metallic material or a ceramic material.

11. The wireless power transfer system of claim 8, wherein the electronic device further comprises:
    a detector configured to detect information about power received in the receiver coil; and
    a transmitter configured to transmit the information to outside the electronic device.

12. The wireless power transfer system of claim 11, wherein the wireless power transfer device further comprises a receiver configured to receive the information from the transmitter, and
    wherein the controller is configured to control the first current and the second current provided by the driver based on the information from the transmitter.

13. The wireless power transfer system of claim 8, wherein the electronic device is configured to store energy received in the receiver coil.

14. The wireless power transfer system of claim 8, wherein the first and second transmitting coils are configured, when having fixed positions and when the receiver coil is above or below the area of overlap and oriented in a plane parallel to the first and second transmitting coils, to generate a magnetic field at the receiver coil having any direction in the plane.

15. The wireless power transfer system of claim 8, wherein the first and second transmitting coils are configured, when having fixed positions substantially in a plane parallel to the first and second transmitting coils, and when the receiver coil is in the plane and oriented parallel to the plane, to generate a magnetic field at the receiver coil having any direction in the plane.

16. A method of transmitting power to an electronic device, the method comprising:
    generating a magnetic field by driving, with AC current provided by a driver, at least one selected from:
    a first transmitting coil of a wireless power transfer device oriented along a first axis, and
    a second transmitting coil of the wireless power transfer device on the first transmitting coil and oriented along a second axis different from the first axis, a nonmagnetic material magnetically decoupling the first transmitting coil from the second transmitting coil being in an area of overlap between the first and second transmitting coils; and
    differentially driving, by the driver, the first and second transmitting coils, by independently controlling amplitudes of AC currents respectively provided to the first and second transmitting coils, to control a direction of the magnetic field,
    wherein the first transmitting coil comprises a first rod and a first wire wound around the first rod,
    wherein the second transmitting coil comprises a second rod and a second wire wound around the second rod,
    wherein the first wire comprises a first sub-coil at one end of the first rod and a second sub-coil at another end of the first rod and spaced apart from the first sub-coil, and
    wherein the second wire comprises a third sub-coil at one end of the second rod and a fourth sub-coil at another end of the second rod and spaced apart from the third sub-coil.

17. The method of claim 16, further comprising inductively generating, via the magnetic field, a current in a receiver coil of the electronic device.

18. The method of claim 17, wherein the generating of the magnetic field comprises setting an amplitude of a first AC current in the first transmitting coil, setting an amplitude of a second AC current in the second transmitting coil, setting a phase of the first AC current, and setting a phase of the second AC current to align the magnetic field of the first and second transmitting coils at the receiver coil with the receiver coil.

19. The method of claim 17, further comprising:
    generating an initial magnetic field and rotating a direction of the initial magnetic field at the receiver coil by:
    driving, with a first AC current, the first transmitting coil over a range of amplitudes of the first AC current, and
    driving, with a second AC current, the second transmitting coil over a range of amplitudes of the second AC current; and
    determining a combination of a first amplitude of the first AC current and a second amplitude of the second AC current that aligns the direction of the initial magnetic field at the receiver coil with the receiver coil.

20. The method of claim 19, wherein the rotating further comprises changing at least one selected from a phase of the first AC current and a phase of the second AC current, and
    wherein the determining of the combination further comprises determining a first phase of the first AC current and a second phase of the second AC current that, together with the first amplitude and the second amplitude, aligns the initial magnetic field at the receiver coil with the receiver coil.

21. The method of claim 19, wherein the determining of the combination further comprises:
    detecting a range of currents generated in the receiver coil during the rotating; and
    determining that the first amplitude and the second amplitude corresponds to a maximum current in the detected range of currents, and
    wherein the generating of the magnetic field comprises:
    driving the first transmitting coil with AC current having the first amplitude; and
    driving the second transmitting coil with AC current having the second amplitude.

22. The method of claim 21, further comprising transmitting information about the detected range of currents from the electronic device to the wireless power transfer device, wherein the determining that the first amplitude and the second amplitude corresponds to the maximum current is performed by a controller.

23. The method of claim 17, further comprising positioning the wireless power transfer device and/or the electronic device such that the receiver coil is oriented in a plane parallel to the first transmitting coil and the second transmitting coil.

24. The method of claim 16, wherein the electronic device is an implantable medical device.

\* \* \* \* \*

UNITED STATES PATENT AND TRADEMARK OFFICE
CERTIFICATE OF CORRECTION

PATENT NO. : 11,990,772 B2
APPLICATION NO. : 17/517518
DATED : May 21, 2024
INVENTOR(S) : Brian R. Dearden et al.

Page 1 of 1

It is certified that error appears in the above-identified patent and that said Letters Patent is hereby corrected as shown below:

In the Claims

In Column 18, Line 38, in Claim 1, delete "cons;" and insert -- coils; --.

In Column 18, Line 50, in Claim 1, delete "sub-con" and insert -- sub-coil --.

In Column 18, Line 52, in Claim 1, delete "s aced a art" and insert -- spaced apart --.

In Column 18, Line 54, in Claim 1, delete "sub-con" and insert -- sub-coil --.

In Column 18, Line 66, in Claim 4, delete "sub coil," and insert -- sub-coil, --.

In Column 18, Line 67, in Claim 4, delete "sub-con" and insert -- sub-coil --.

Signed and Sealed this
Seventeenth Day of September, 2024

Katherine Kelly Vidal
*Director of the United States Patent and Trademark Office*